(12) United States Patent
Fischer

(10) Patent No.: US 6,213,771 B1
(45) Date of Patent: Apr. 10, 2001

(54) INCREMENTALLY ADJUSTABLE ENDODONTIC INSTRUMENTS

(75) Inventor: Dan E. Fischer, Sandy, UT (US)

(73) Assignee: Ultradent Products, Inc., Sandy, UT (US)

( * ) Notice: Subject to any disclaimer, the term of this patent is extended or adjusted under 35 U.S.C. 154(b) by 0 days.

(21) Appl. No.: 09/425,857

(22) Filed: Oct. 22, 1999

(51) Int. Cl.[7] ........................................ A61C 5/02
(52) U.S. Cl. ............................ 433/75; 433/102; 433/165
(58) Field of Search ........................... 433/102, 165, 433/75

(56) References Cited

U.S. PATENT DOCUMENTS

| | | | |
|---|---|---|---|
| 3,562,913 | 2/1971 | Saffro | 32/57 |
| 3,713,221 | 1/1973 | Malmin | 32/57 |
| 3,772,791 | 11/1973 | Malmin | 32/57 |
| 3,924,334 | 12/1975 | Lentine et al. | 32/57 |
| 3,938,253 | 2/1976 | Barnard et al. | 32/40 R |
| 3,961,422 | 6/1976 | Riitano et al. | 32/57 |
| 3,962,791 | 6/1976 | Zdarsky | 32/57 |
| 4,182,040 | 1/1980 | Bechtold, Jr. | 433/77 |
| 4,268,251 | 5/1981 | Takasugi et al. | 433/75 |
| 4,280,808 | 7/1981 | Johnsen et al. | 433/77 |
| 4,340,364 | * 7/1982 | Deemer | 433/75 |
| 4,609,352 | 9/1986 | Riitano | 433/102 |
| 4,836,780 | 6/1989 | Buchanan | 433/102 |
| 4,904,185 | 2/1990 | McSpadden | 433/164 |
| 5,035,617 | 7/1991 | McSpadden | 433/102 |
| 5,154,611 | 10/1992 | Chen | 433/77 |
| 5,498,158 | * 3/1996 | Wong | 433/102 |
| 5,516,287 | 5/1996 | Zdarsky | 433/102 |

FOREIGN PATENT DOCUMENTS

| | | | |
|---|---|---|---|
| 929867 | * 7/1955 | (DE) | 433/102 |
| 2925602 | * 1/1981 | (DE) | 433/75 |
| 2 022 475 | 12/1979 | (GB) . | |
| 2059778 | * 4/1981 | (GB) | 433/102 |

* cited by examiner

Primary Examiner—Todd E. Manahan
(74) Attorney, Agent, or Firm—Workman, Nydegger & Seeley

(57) ABSTRACT

A dental instrument is provided for use in an endodontic procedure which has a file extending from a handle configured to enable the working length of the handle to be varied. The handle of the instrument is adapted to be received in and to be releasbly held by a chuck or collet of an endodontic handpiece head. Both the handles and chucks are adapted to enable the handles to be appropriately positioned in the chuck of a dental handpiece head at various positions to yield a desired working length and to then be secured. The rim around the chuck is preferably configured to act as a stop during use of the handpiece. The handle is most useful when configured with incremental adjustment indicators, preferably in uniform increments, such that the working length can be determined by viewing the indicators.

23 Claims, 12 Drawing Sheets

INCREMENTALLY ADJUSTABLE ENDODONTIC INSTRUMENTS

BACKGROUND OF THE INVENTION

1. The Field of the Invention

The present invention relates generally to dental instruments. More particularly, the present invention relates to an endodontic instrument for use in an endodontic procedure that has an adjustable working length.

2. The Relevant Technology

In order to preserve a tooth that has diseased pulp material therein, it is necessary to prevent bacterial proliferation within the pulp canal of the tooth by removing the diseased or necrotic pulp material from the pulp cavity or root canal. After the pulp material has been removed or extirpated from a tooth, the pulp cavity or root canal is typically filled or obturated with an inert material before being sealed off with an inert sealer of an aseptic material in order to prevent future infection of the tooth root. This procedure is referred to as root canal therapy.

During root canal therapy, it is essential that the entire root canal, including the root tip, be cleaned and filled to eliminate all organic matter contained within the root canal. The typical method followed for root canal therapy is to open the tooth to the pulp chamber and then work down to the root end. Root canal cleaning or preparation is generally achieved by hand or mechanical instrumentation with files or bits that are configured to bore and/or cut. In order to gain access to the pulp chamber in a tooth, a hole is drilled through the tooth to the pulp chamber and subsequently widened. A variety of endodontic instruments are then used to enlarge and clean out the root canal to remove all the pulp tissue.

Conventional dental instruments used during root canal therapy such as various file instruments generally include a thin, flexible, metal shaft or file with an abrasive surface or sharp edges, which enables efficient cleaning of the root canal. A handle or hub end is securely affixed at one end of the file instrument and is adapted for gripping by an operator or attachment to a mechanical device such as a dental drill.

It is often necessary to repeatedly insert and remove various file instruments into the root canal of a tooth during root canal therapy. Extreme care must be taken to prevent penetration of such file instruments beyond the root canal apex in order to avoid injury and possible infection of the adjacent periodontal tissue and bone structure. The file must be inserted no more than a specific maximum distance inside the root of the tooth. The occurrence of errors in depth penetration of the file into the root canal, either too deep or too shallow, are the major cause of failure in endodontic procedures. Thus, it is important in the preparation of the root canal to control the working length of the file utilized. Since it is physically impossible for a practitioner to see inside the tooth to the root apex, a determination must be made as to how far the file can enter the root.

Before a file instrument is inserted to remove the pulp material, the length of the root canal is determined to identify a suitable working length for the file instrument. Generally, the working length is the distance from a fixed reference position on the crown of a tooth to or near the apical constriction opening of the root canal. Typically, a practitioner initially ascertains the depth through which the various sized root canal instruments should penetrate into the root canal by utilizing an x-ray of the tooth. A full scale x-ray of the tooth is taken and the insertion distance is measured on the developed x-ray photograph by measuring the length of the tooth involved, as well as the length of the root canal therein.

A significant problem that can result from root canal cleaning is apical perforation from insertion of a file or shaft of a file instrument to the apex of the root canal. Perforating the apex can result from an error in estimating or measuring the length of a root canal. Similarly, the apex can be perforated by extrusion of infected pulp material through the apex due to the force exerted by the file on the pulp material as the file is pushed downward to reach the apex. In addition to exposing the tissue surrounding the tooth to the infected pulp material, apical perforations also substantially complicate subsequent filling of the root canal with a filling or obturating material.

Various techniques and devices have been developed for limiting the depth of penetration of dental instruments to the root canal tip. For example, once the length of the root canal has been determined, it is possible to use a dental instrument having a file extending beyond the handle by the predetermined maximum allowable length.

More commonly, an adjustable stopper has been typically placed over each dental instrument along the shaft or file so that the distance between the tip of the instrument and the stopper equals the distance between the top or the occlusal surface of the tooth and the apex of the root canal. Thus, the stopper sets the root canal instrument to the proper length or penetration depth for the root canal. The stopper located at the proper point along each root canal instrument intended to be used ensures that the instrument is inserted the proper depth into the root canal.

Examples of instruments utilizing stoppers are shown in FIG. 1 and FIG. 2 respectively at 10 and 20. Instrument 10 has a peanut-shaped handle 12 which is particularly adapted to be gripped by a practitioner during a root canal procedure. Handle 12 is accordingly typically used for manual filing. Instrument 20 has a latch handle 22 for attachment to an endodontic handpiece for rapid rotation as shown in FIG. 3 at 60. A stopper 40 is shown positioned on file 14 of instrument 10 and on file 24 of instrument 20. Such stoppers are typically formed of a simple block of rubber or plastic material, or constructed of a housing and a compression spring. In addition to a single stopper as shown in FIG. 1 and FIG. 2, several movable stoppers may be utilized and positioned on the shaft such that one stopper abuts the handle. An additional example of an endodontic device utilizing stoppers is disclosed in U.S. Pat. No. 5,154,611 to Chen.

The position of the stopper on the file determines the working length of the instrument, which is the length of the file to be inserted into the tooth during treatment. As shown in FIG. 4, stopper 40 prevents further penetration of file 24 into the root canal of the tooth when the bottom surface of stopper 40 abuts the occlusal surface of the tooth 90 being treated, such as the incisal edge or cusp tip. In this manner, when the dental instrument enters the root canal, the dentist can limit insertion by observing the contact of the stopper at the edge of the tooth.

Since a variety of file instruments are used throughout the root canal procedure, conventional practice has been to individually measure and position the stoppers on the various implements used. It is frequently necessary for the dentist to fit a stopper on the dental instrument while the patient's mouth is held open. Thus, it is desirable that the operation be carried out as fast as possible. At the same time it is essential that stoppers be placed with perfect accuracy, as otherwise the possibility of poking the instrument beyond the tooth is presented.

The problems with the conventional stopper procedure are numerous. The individual measurement and placement of the stoppers on the dental instruments is very time1 consuming and at times somewhat inaccurate. Each individual instrument and its stopper must be separately gauged against a separate scale or ruler and then individually set to the length indicated in an x-ray photograph. This procedure can involve inherent inaccuracies and a great deal of time and inconvenience to the dentist. In addition, there is also the potential for introduction of contaminants on the instrument during placement of a stopper thereon.

Further, the stoppers can be easily displaced or can slip from their intended position on the file instrument during use within the limited area of a patient's mouth and considering the relatively small size of the instruments involved. This can result in perforation of the apex of a tooth from failure of a stopper to remain at a predetermined position. It can also be difficult for the endodontist to precisely judge when the stopper has reached the surface of the tooth. Additionally, rubber stoppers may also be both flexible and movable and can therefore allow the file to proceed deeper into the root canal than may be desired.

Other devices have also been developed to limit the penetration of dental instruments into a root canal. For example, screw threads have been placed on the shaft of a file, with a nut threaded onto the file to act as a stopper. The manipulation of the file within a patient's mouth, however, can easily result in the nut being moved on the shaft.

In U.S. Pat. No. 4,028,810 to Vice, a root canal file is disclosed that includes a handle portion adjustably mounted in telescoping relation to the shaft of an elongated tool, with cooperating grooves in the shaft and handle preventing relative movement therebetween during use. The grooves around the shaft cooperate with mating ridges or grooves within the jaws of a tightening chuck on the handle to firmly interlock the handle and the shaft in any desired adjustment position.

Another endodontic instrument, disclosed in U.S. Pat. No. 4,165,562 to Sarfatti, includes a threaded base with a locking structure thereon and an elongated file projecting outwardly from the base. A threaded sleeve which acts as a stopper receives the base to facilitate longitudinal adjustment of the file relative to the sleeve. A plastic cap fits over the combination of the file and the sleeve and is imprinted with a plurality of graduations thereon to indicate the distance that the bottom of the file extends from the bottom of the sleeve.

While the above devices can limit the penetration of dental instruments into a root canal they are not adequately simple to use and manufacture. More importantly, however, conventional dental instruments do not provide a secure stopping capability while simultaneously enabling an instrument to be used with varying working lengths. Accordingly, there is a need for an improved endodontic device that overcomes or avoids the above problems.

SUMMARY AND OBJECTS OF THE INVENTION

The present invention has been developed in response to the present state of the art and, in particular, in response to problems and needs that have not been fully or completely solved by currently available endodontic instruments. It is an object of the present invention to provide dental instruments which may be positioned in an endodontic handpiece head such that the instruments have varying working lengths for use during an endodontic procedure such as root canal therapy. It is also an object of the present invention that such instruments be simple to use and manufacture. It is an additional object of the present invention that such dental instruments provide a secure stopping capability while simultaneously enabling an instrument to be used with varying working lengths. It is a further object of the present invention that the length variations be identifiable by viewing the instrument in the chuck of an endodontic handpiece head. Finally, it is an object of the present invention that the working length of the instrument be variable in uniform increments.

Features of the invention are briefly described hereinbelow. The dental instrument includes a file extending from a handle configured to enable the working length of the handle to be varied. The handle of the instrument is adapted to be received in and to be releasbly held by a chuck or collet of an endodontic handpiece head. Both the handles and chucks are adapted to enable the handles to be appropriately positioned in the chuck of a dental handpiece at various positions to yield a desired working length and to then be secured.

The need for rubber stoppers is eliminated since the handle is securely held by the chuck such that the instrument has varying working lengths which remain securely fixed during an endodontic procedure. Accordingly, a practioner can use the present invention without worrying that the working length will change during use due to slipping of a rubber stopper or movement of the handle relative to the chuck. Additionally, the rim around the chuck is preferably configured to act as a stop during use of the handpiece in an endodontic procedure.

In using the dental instrument of the invention, an instrument is selected which has an approximately appropriate file length. The working length of the instrument can then be varied by positioning the handle of the instrument into a chuck of a handpiece and then securing the handle in the chuck to provide a desired working length. More particularly, the instrument is adjusted to a desired position with respect to the chuck by pushing the handle of the instrument further into the chuck or by pulling the instrument out until the correct position is obtained. This eliminates the need for multiple instruments having many different working lengths.

The chuck has retention arms which are preferably rounded in order to be applied in a mated configuration with the flat cylindrical surfaces of the handle. The retention arms of the chuck are configured to press against the handle in order to hold the chuck.

The handle preferably has incremental adjustment indicators such that the working length can be determined by viewing the incremental adjustment indicators. The indicators may be distinctive portions of the handle. The distinctive sections preferably have uniform lengths, particularly at the bottom of the handle. For example, the bottom of the handle may have a section, referred to herein as a gripping section, which is configured for engagement with the retention arms of the chuck and which is sandwiched between two distinct sections. More particularly, the gripping section may be sandwiched between a bevelled section which tapers toward the file and a section which is slightly recessed compared with the gripping section. Such sections preferably have the same length such as 1 mm to enable the user to move the handle in distinct increments which are uniform.

The handle may be alternatively configured with markings which extend around the perimeter of the handle as bands or as lines around only a portion of the perimeter. The markings may all be the same color or each marking may have a different color. Such markings may be printed onto the handle or formed by other suitable methods such as two color molding processes. Like the distinct sections of the handle discussed above, the markings are preferably uniformly spaced to provide uniform incremental adjustment indicators.

Alternatively, the handle and retention arms may also be configured such that it is possible to move the handle only in discrete uniform increments. It is also possible use a handle with no incremental adjustment indicators and to then use a gauge or similar device to measure the working length of the instrument.

The file of the instruments may have any suitable configuration. However, the files are preferably configured for use in cleaning the operative middle portion of the root canal which is the portion of the anatomical root canal above the apical portion. Other instruments can then be used to clean the apical portion. The methodology described herein for cleaning the operative middle portion involves using the contours of the operative middle portion as a guide for movement of the file. The file is accordingly moved around the perimeter of the root canal or moved from side to side while the instrument is flexed against the root canal surfaces. This movement is rather aggressive so the methodology is particularly benefited by the secure stopping action provided by the rim of the endodontic handpiece head.

The present invention is advantageous in that the length of the dental instrument can be quickly adjusted in a simple manner and such instruments are simple to manufacture. This ability is further enhanced by the ability to identify the length variations by merely viewing the instrument in the chuck of an endodontic handpiece head when the handle has incremental adjustment indicators, particularly uniform incremental adjustment indicators. Another advantage is the elimination of the need for rubber stoppers through the use of the rim of the endodontic handpiece head. Additionally, it decreases the number of instruments needed for completing conventional root canal therapy procedures as some practioners prefer to have as many instruments having fixed lengths as are necessary to work within typical root canals without rubber stoppers.

These and other objects, features and advantages of the present invention will become more fully apparent from the following description and appended claims, or may be learned by the practice of the invention as set forth hereinafter.

BRIEF DESCRIPTION OF THE DRAWINGS

In order to understand the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE INVENTION

The present invention is directed to an endodontic instrument configured to have a working length that can be varied.

More particularly, the working length is varied by securing the handle of an endodontic instrument in a chuck or collet of a dental handpiece at various positions. Both the handles and chucks are adapted to enable the handles to be appropriately positioned to yield a desired working length and to then be secured. Additionally, the rim around the chuck is preferably configured to act as a stop during use of the handpiece in an endodontic procedure.

Root canal therapy typically involves cleaning and enlargement of the root canal prior to applying an inert sealant. In many endodontic operations, it is necessary to successively insert an elongated instrument into, and then pull the same from, the root canal of a tooth in order to thoroughly remove any inflamed or necrotic tissue therein and properly enlarge the root canal. The length of the instrument is important as the endodontist must be careful not to extend the instrument beyond the apex of the root canal in a tooth to avoid exposing the tissue surrounding the tooth to infected material or pushing infected matter into the surrounding tissue. An appropriate length is determined by taking an x-ray or a sonic reading of the tooth to be treated.

FIGS. 5–9 depict examples of instruments suitably adapted for use with an endodontic handpiece to provide varying working lengths. Each instrument has two primary components including a handle and an elongated working member or file configured to extend from the handle. The file can have any suitable configuration for use in root canal therapy or other endodontic procedures. Each instrument is discussed in detail hereinbelow.

In using the dental instrument of the invention, an instrument is selected which has an approximately appropriate file length. The working length of the instrument can then be varied by positioning the handle of the instrument into a chuck of a handpiece and then securing the handle in the chuck to provide a desired working length. More particularly, the instrument is adjusted to a desired position with respect to the chuck by pushing the handle of the instrument further into the chuck or by pulling the instrument out until the correct position is obtained. The instrument can then be effectively used during an endodontic procedure. Use of the instruments with handpieces is discussed hereinbelow in relation to FIGS. 11–13.

Figures 5, 6, 7, 8, 9:
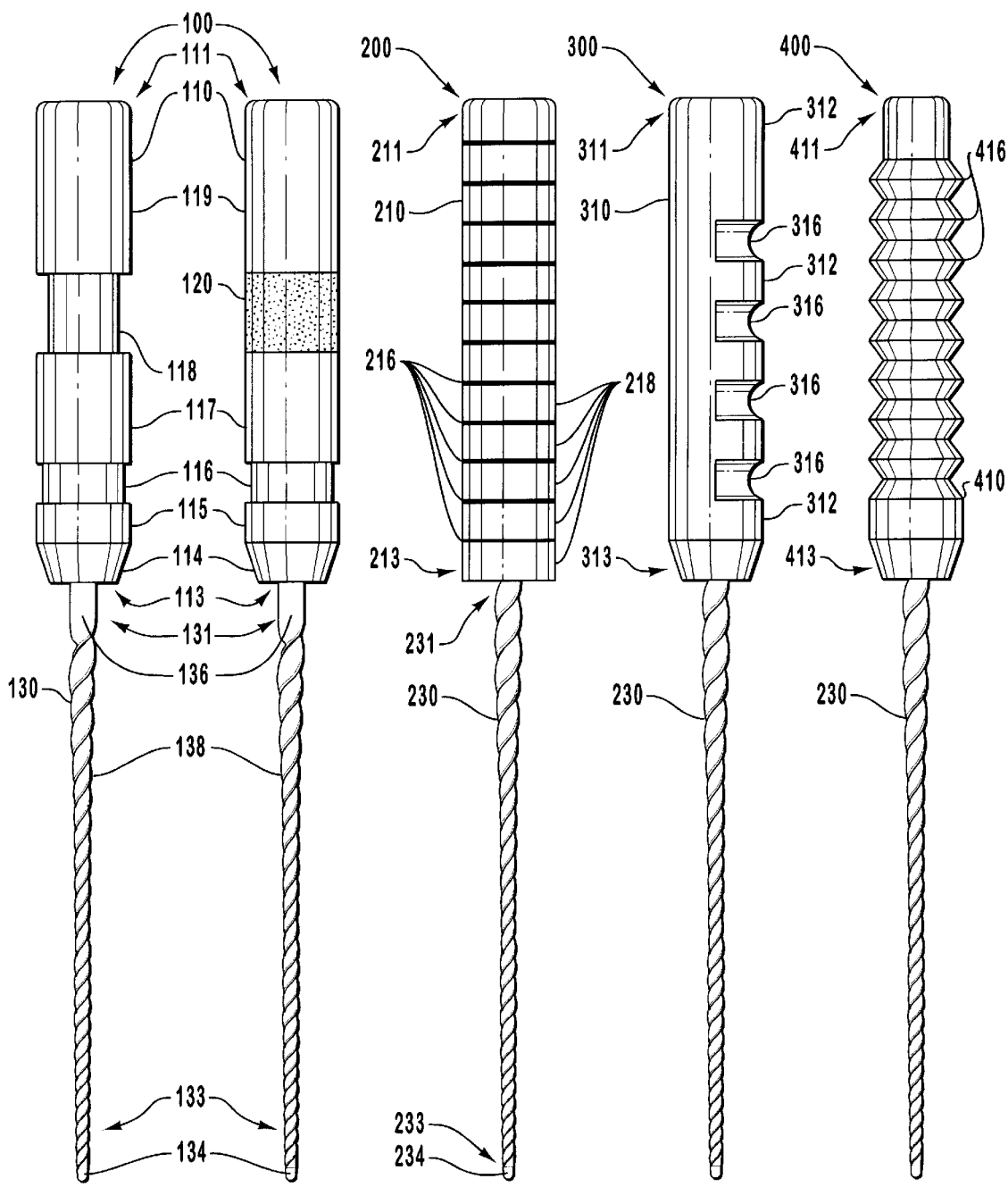
FIG. 5 is a perspective view of an instrument having a handle according to the present invention.
FIG. 6 is a perspective view of the instrument shown in FIG. 5 having an identification band.
FIG. 7 is a perspective view of another embodiment of a instrument having a handle configured in accordance with the present invention.
FIG. 8 is a perspective view of another embodiment of the present invention.
FIG. 9 is a perspective view of another embodiment of the present invention.

FIGS. 5–6 depict an endodontic dental instrument 100 according to one embodiment of the invention. The dental instrument 100 includes a handle 110 and a file 130 which extends from handle 110.

Handle 110 has a top end 111 and a bottom end 113. Handle 110 has several distinct sections which each have an incremental length. Beginning at top end 111, there is a bevelled section 114 followed by a bottom gripping section 115. A shallow recess 116 is located between bottom gripping section 115 and a middle gripping section 117. FIG. 5 shows a band groove 118 interposed between middle gripping section 115 and top gripping section 119 of handle 110. Handle 110 is one example of a handle means for operatively moving a file to facilitate an endodontic procedure. The other handles disclosed herein are also examples of such handle means.

Instrument 100 as shown in FIG. 6 differs from that shown in FIG. 5 by the identification band 120 positioned within band groove 118. Instruments such as instrument 100 are typically sold in sets wherein the files of the instruments have different lengths. To identify the length of file 110, identification band 120 is provided which preferably has a particular color associated with the length of the file. Accordingly, a set of instruments may be provided which have files of varying lengths and differently colored identification bands to indicate the length of the files in the set. Identification band 120 is an example of a means for visually identifying the length of the file.

As indicated above and as discussed in greater detail hereinbelow in reference to endodontic handpieces, a handle of an instrument is moved within the chuck of an endodontic handpiece to increase or decrease the working length of the instrument. After determining the root canal length and the working length needed to work in a desired manner within the root canal, the file length is identified which approximately corresponds with the length determined as necessary for working in the root canal. More particularly, an instrument is selected having an identification band which indicates that the length of the instrument is slightly less than the determined length of the root canal or the length determined as being necessary.

After selecting an appropriate instrument, the demarcations on the handle, which are sections having incremental lengths, can be used to fine tune the working length of the instrument. For example, bevelled section 114, bottom gripping section 115 and shallow recess 116 are each 1 mm long, thereby enabling a user to adjust the working length in 1 mm increments. If an adjustment is needed which is greater than 3 mm, it is preferable to use a different instrument having a file with a greater length. However, middle gripping section 117 has a length of 3 mm so handle 110 can be extended even farther out of a chuck. It is even possible to extend handle 110 out of a chuck such that the chuck holds only top gripping section 119 or top gripping section 119 and identification band 120. Identification band 120 and top gripping section 119 have lengths which are respectively 2 mm and 4 mm. Identification band 120 is sufficiently thick that its surface is essentially level with that of middle gripping section 117 such that when it is gripped within a chuck, pressure can be applied to the band groove 118 via identification band 120 as well as to top gripping section 119 and any sections below which are level therewith and within the chuck.

Two or more sections such as bevelled section 114, bottom gripping section 115, shallow recess 116, middle gripping section 117, band groove 118 and top gripping section 119 are examples of incremental adjustment indicators. Such indicators are also examples of incremental adjustment indicator means for indicating the working length of an instrument once the handle is held within a chuck of an endodontic handpiece head. Sections which all have the same incremental length such as bevelled section 114, bottom gripping section 115, shallow recess 116 which all have a length of 1 mm are examples of uniform incremental adjustment indicators. Such uniform incremental adjustment indicators are also examples of uniform incremental adjustment indicator means.

If handle 110 is held in a chuck such that part of middle gripping section 117 is extending out from a chuck and the remainder is held within the chuck, then it may be necessary to measure the working length of instrument 100 in order to exactly identify the working length. Similarly, if the handle is completely uniform in cross-sectional shape and has no printed demarcations to indicate incremental variations in length it is not possible to accurately determine the length by viewing it. Accordingly, to identify the working length of an instrument with such a handle, it is necessary to measure the working length of the instrument.

Figure 10A:
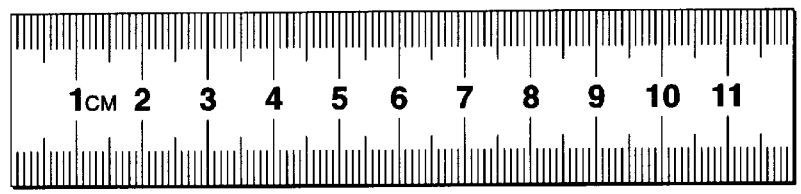
FIG. 10A is a perspective view of a ruler which can be used to measure the working length of an endodontic instrument.

There are several devices and methods which are useful for measuring the length of endodontic instruments. For example, a ruler having a millimeter scale offers a simple mechanism to quickly measure the working length as shown in FIG. 10A and as disclosed in U.S. Pat. No. 3,772,791 issued to Malmin. The ruler may, for example, be transparent or be stainless steel. The ruler may also be configured to be worn as a ring on a thumb or finger. An example of such a finger worn ruler is disclosed in U.S. Pat. No. 4,976,615 issued to Kravitz and in U.S. Pat. No. 4,280,808 issued to Johnsen et al. The above patents are all incorporated by reference.

Figure 10B:
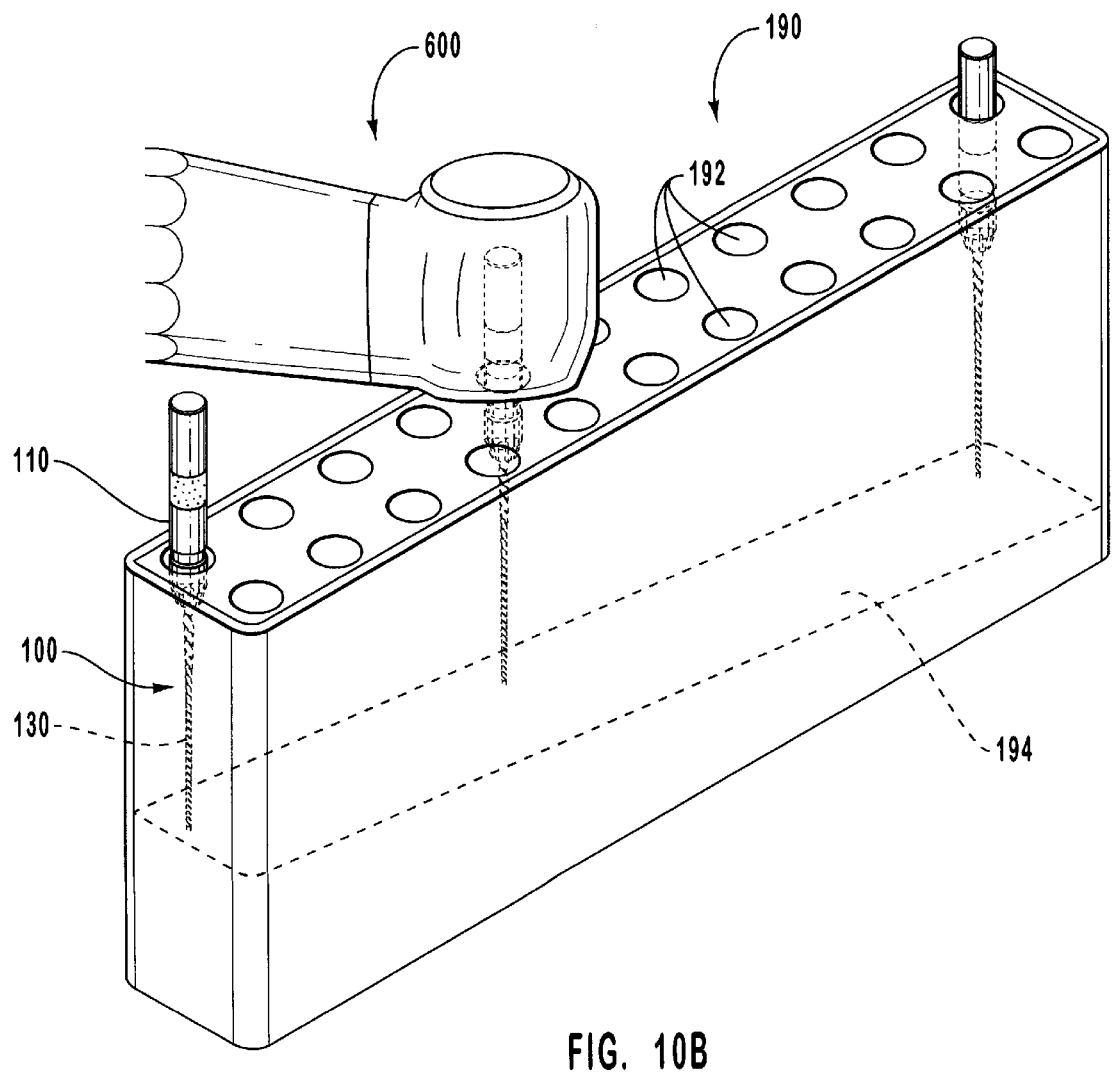
FIG. 10B is a perspective view of a gauge which can be used to measure the working length of an endodontic instrument.

There are also many gauges presently sold which enable a practioner to insert an instrument and obtain a measurement of the working length. One example of such a gauge is a measuring block as shown in FIG. 10B at 190 having a plurality of holes 192 in the top of the block which extend into a chamber defined by a wedge 194. Once an instrument is inserted into a hole such that the tip encounters the tapered chamber, the length is identifiable by the position of the hole relative to the other holes. Similarly, U.S. Pat. No. 3,938,253 issued to Barnard et al. discloses the use of two circular plates arranged in coaxial spaced apart disposition with one plate having a series of through holes therein to each receive a respective instrument with the tip thereof resting on the other plate. Additional examples of appropriate gauges are disclosed in U.S. Pat. No. 4,182,040 issued to Bechtold and in U.S. Pat. No. Des. 292,021 issued to Stoll. The above patents are all incorporated by reference. Such rulers and gauges are examples of means for measuring the working length of an endodontic instrument.

The handle may have any appropriate length which enables it do be moved within the chuck and then to be securely held. For example, handle 110 may be about 12 mm in length. The width of the handle is preferably minimized to enable the endodontic handpiece to also have as small of a head as possible for enhanced maneuverability within a patient's mouth. The handle 110 can be made from any suitable material such as various metals or plastics.

File 130, which extends from top end 111 of handle 110, is an example of an elongated working member adapted for use in an endodontic procedure. The elongated working member may have any cutting configuration known for use as a reamer, bit, broach, or as a similar instrument. File 130 has a proximal end 131 opposite a distal insertion end 133 which terminates at a narrow tip 134. File 130 has a shank portion 136 which transitions to an abrading portion 138. The visible portion of file 130, which is the portion extending from handle 110 is the working portion of file 24. The working length of the instrument, however, is determined by the manner in which the handle is positioned in a chuck of a handpiece.

The diameter of file 130 is small enough so that file 130 can be easily inserted into a root canal of a tooth during an endodontic procedure. Generally, file 130 has a diameter in a range from about 0.06 mm to about 2 mm. File 130 is preferably made from a high strength resilient metal, such as stainless steel, capable of sufficient flexing to follow the normal curvatures of a root canal in a tooth and has an abrasive surface. File 130 can, however, be made of any suitable material such as nickel/titanium. File 130 is an example of a file means for removing and cleaning pulp material from a root canal during an endodontic procedure in an abrasive action. The other files disclosed herein are also examples of such file means.

FIG. 6 depicts an endodontic dental instrument 200 according to another embodiment of the invention. Dental instrument 200 includes a handle 210. Handle 210 has a top end 211 and a bottom end 213.

Handle 210 has a series of gradient markings 216 formed thereon. Markings 216 may be spaced at any desired increment such as in 0.5 mm or in 1 mm increments. The gradient markings 216 are used to make incremental adjustments of handle 210 to a desired position with respect to a chuck of an endodontic handpiece when the dental positioned for use in an endodontic procedure. Gradient markings 216 may all be the same color or each band may have a different color. Gradient markings 216 may be printed onto handle 210 by any suitable method. Additionally, when handle 210 is formed from plastic, two color molding processes may be used such that gradient markings 216 have a different color than the remainder of handle 210. While the gradient markings are shown extending around the perimeter of the handle, the markings may also be hatch marking which appear on only a portion of the perimeter such that the markings are viewable from a side of the handle.

Gradient markings 216 spaced uniformly as shown in FIG. 7 are additional examples of uniform incremental adjustment indicators and uniform incremental adjustment indicator means. Note, however, that gradient markings can also be formed on handle 210 in nonuniform increments such as 1 mm, 1 mm, 1 mm and then 2 mm. While such a combination as a whole is not uniform it does include some uniformly spaced gradient markings. Such a combination is accordingly an example of nonuniform incremental adjustment indicators as well as incremental adjustment indicators which include uniform incremental adjustment indicators.

The sections of handle 210 identified at 218 are each separated by a gradient marking and each have a uniform length. As indicated above, the uniform length of the sections may, for example, be 1 mm as shown. The sections may also have submarkings to indicate subincremental lengths such as 0.5 mm lengths.

A handle shaped like handle 210 without gradient markings 216 is also within the scope of the present invention. Such a handle without gradient markings is able to move within a chuck to adjust the working length of the instrument. However, it would be necessary to measure the working length of the instrument since it would not be possible to merely view the instrument and determine the working length as in other embodiments.

Instrument 200 has a file 230 which extends from top end 211 of handle 210. File 230 has a proximal end 231 opposite a distal insertion end 233 which terminates at a narrow tip 234. The entire visible portion of file 230 is configured to abrade. The portion of file 230 located within handle 210, which is not shown, may be configured like a shank or be configured to optimally interlock or anchor file 230 in handle 210.

Another embodiment of a suitable instrument is shown at 300 in FIG. 7. Instrument 300 has a handle 310 which has a top end 311 and a bottom end 313. Instrument 300 also has a file 230 which extends from top end 311 of handle 310.

Handle 310 has a series of grooves 316 located on one side of handle 310 which are in uniform increments. The remainder of handle 310 is a gripping section 312. Grooves 316 may be in any suitable increments such as in 1 mm increments. Grooves 316 may be formed by any suitable method. For example, handle 310 may be molded in a configuration such that it appears as shown. Additionally, grooves 316 may be formed by removing segments from a precursor to handle 310 by etching the surface or lathing a metal handle precursor. Similarly, a precursor handle can be rotated and brought into contact with a knife or suitable implement for removing segments thereof.

While grooves 316 are shown as only partially encircling the circumference of handle 310, it should be understood that grooves can be formed around the entire circumference of handle 310. Additionally, grooves 316 need not be curved as shown. The grooves may be replaced by recesses such as shallow recess 116 which have shallow walls which are perpendicular to the surfaces of the gripping sections. Grooves 316 and recesses as described above in relation to handle 310 are additional examples of uniform incremental adjustment indicators and uniform incremental adjustment indicator means.

FIG. 8 depicts another embodiment of an instrument at 400 having a handle 410 and a file 230 extending from a top end 411 of handle 410. Handle 410 has ridges 416 positioned at uniform increments along its length from top end 411 to bottom end 413 of handle 410. Handle 410 can be formed as shown by essentially the same methods used in the formation of handle 310. For example, handle 410 can be molded such that it has ridges 416 or the sections between ridges 416 can alternatively be removed by etching, cutting or lathing when handle 410 is formed from metal. While ridges 410 are shown having pointed tops or peaks, ridges 410 can also be formed to have rounded or sloped tops such that a chuck has a greater surface contact with the handle to hold the handle in position. It may, however, be more difficult to determine the working length of a handle having sloped ridges by merely viewing the instrument as the increments may not be as easily identified. Accordingly, an embodiment having sloped ridges may also have gradient markings to ensure that the length can be quickly determined. Ridges 416, as described above in relation to handle 410, are additional examples of uniform incremental adjustment indicators and uniform incremental adjustment indicator means.

Figure 11A:
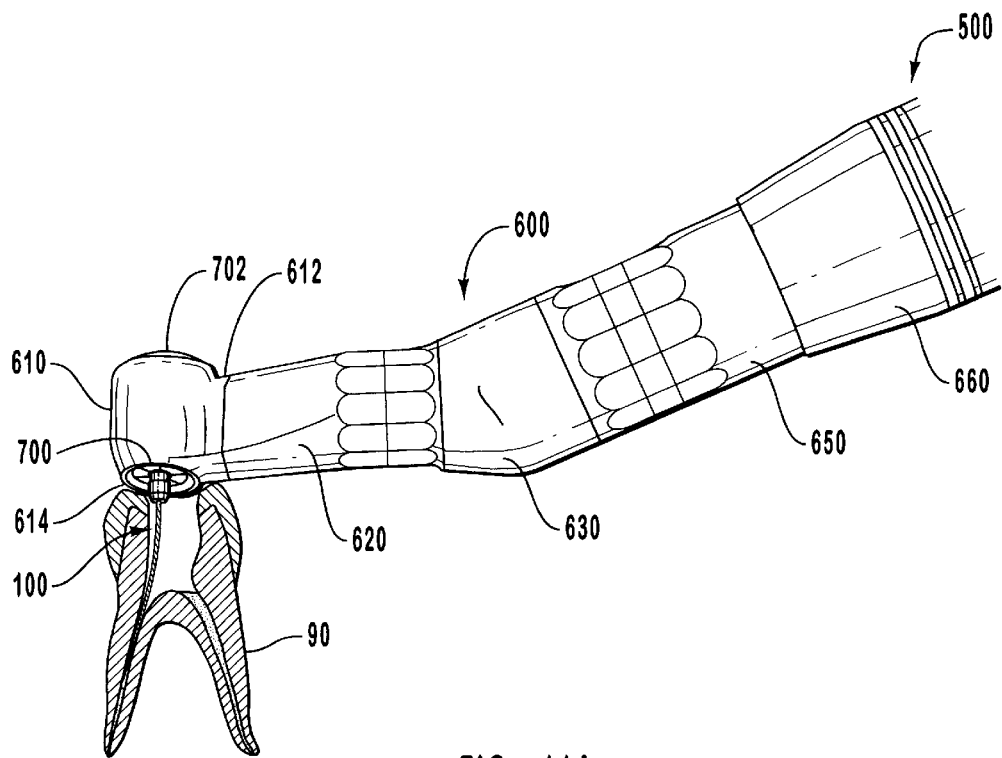
FIG. 11A is perspective view of a handpiece having a chuck which holds an instrument as the instrument is moved within a tooth, which is shown in a cross-sectional view.
Figure 11B:
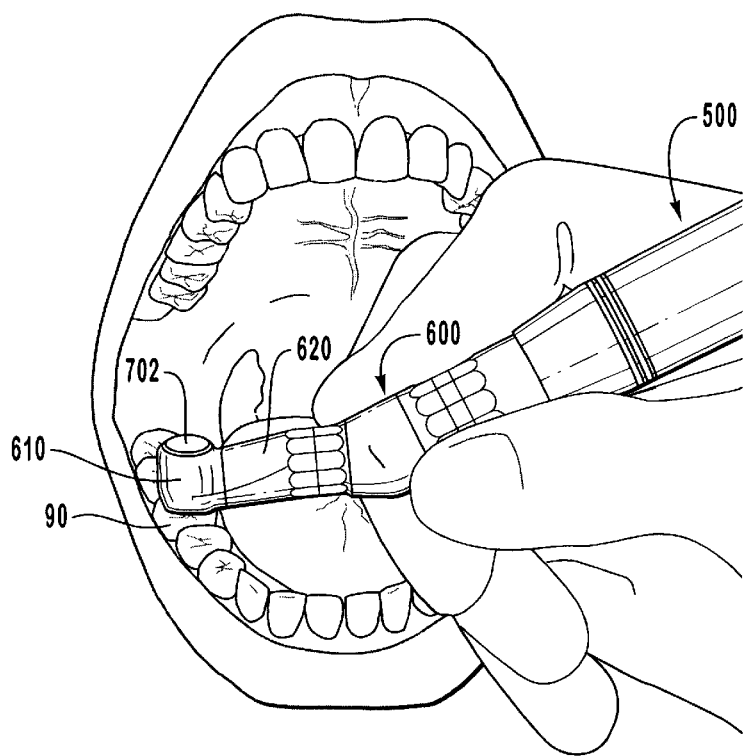
FIG. 11B is a perspective view of the endodontic handpiece shown in FIG. 11A being used in an endodontic procedure.
Figure 11C:
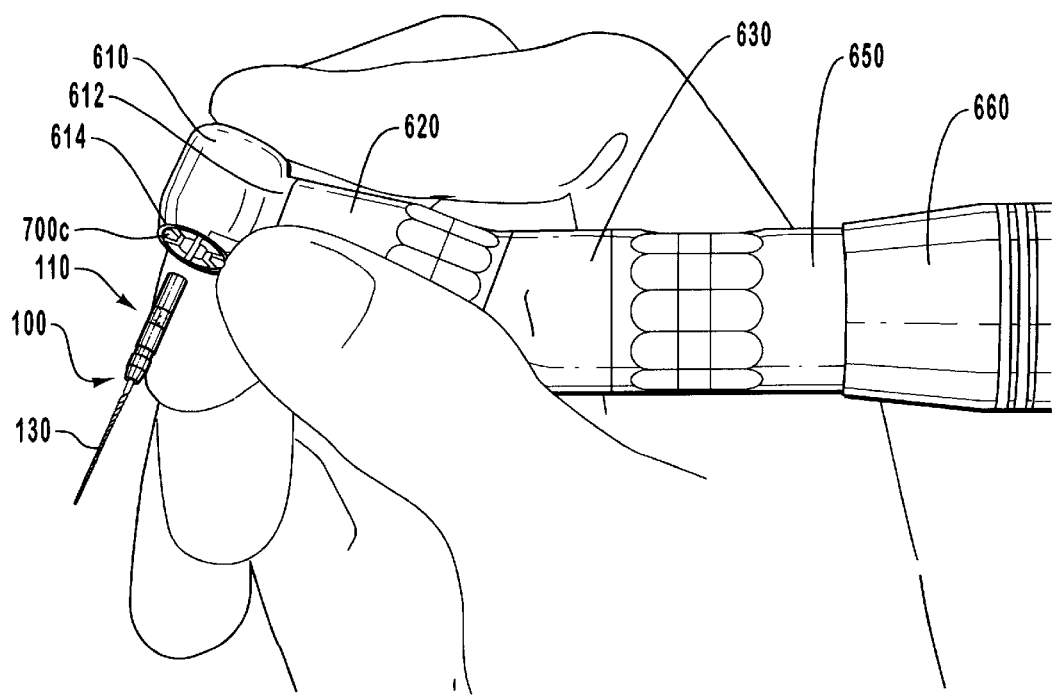
FIG. 11C is a perspective view of a user's hand depressing a cap to lower the chuck into an open position to receive the handle of the instrument.
Figure 11D:
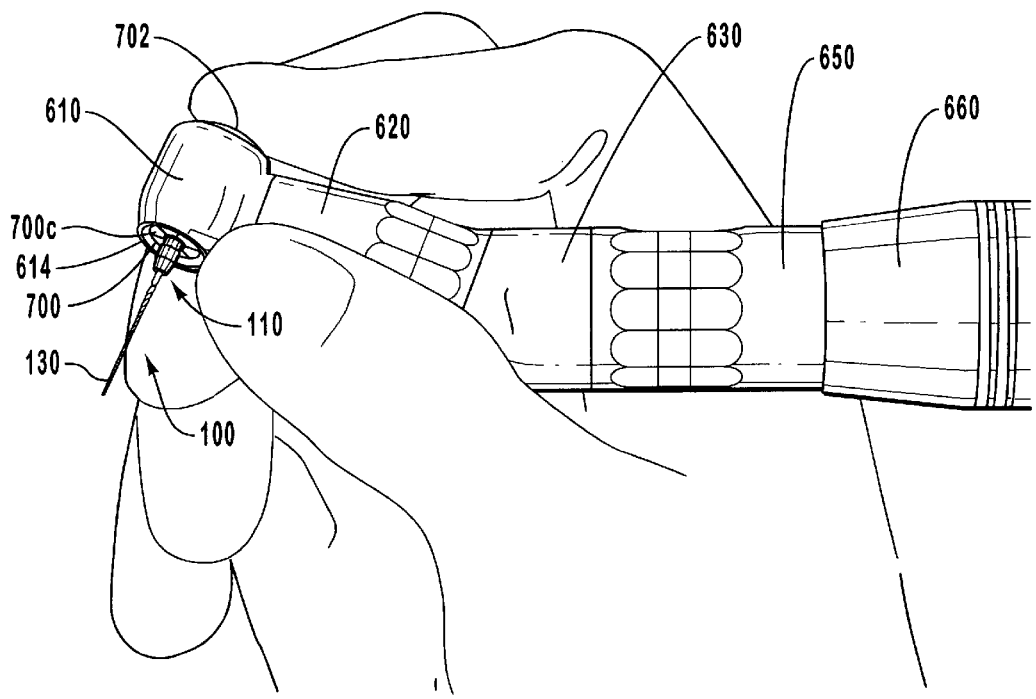
FIG. 11D is a perspective view of a chuck in a closed or engaged position securely holding the handle of the instrument after a cap has been released.
Figure 11E:
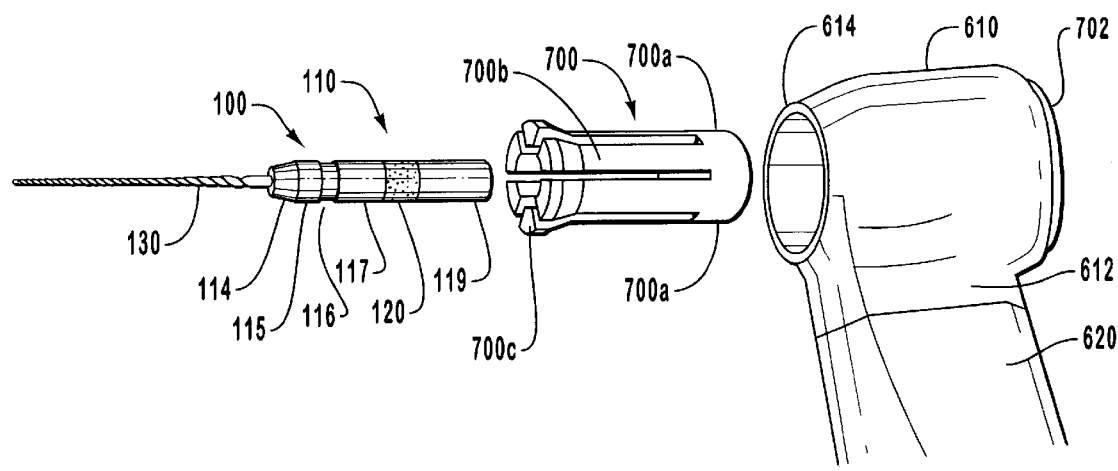
FIG. 11E is an exploded perspective view of a head element of an endodontic handpiece head, a chuck and an instrument.
Figure 12:
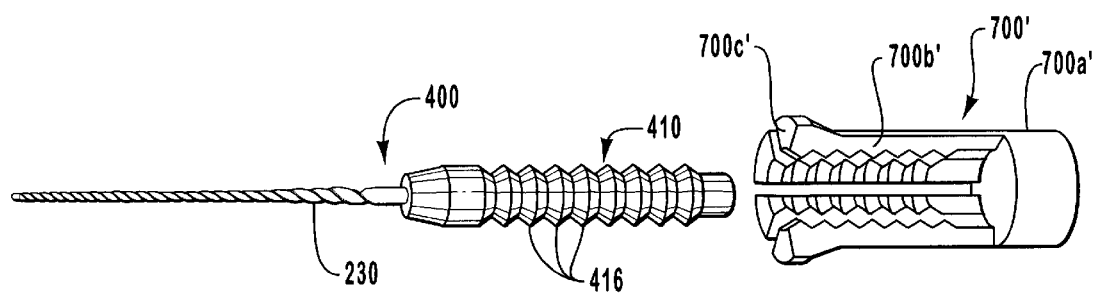
FIG. 12 is an exploded perspective view of the head element of an endodontic handpiece head as shown in FIG. 11E, another embodiment of a chuck and the instrument as shown in FIG. 9.
Figure 13A:
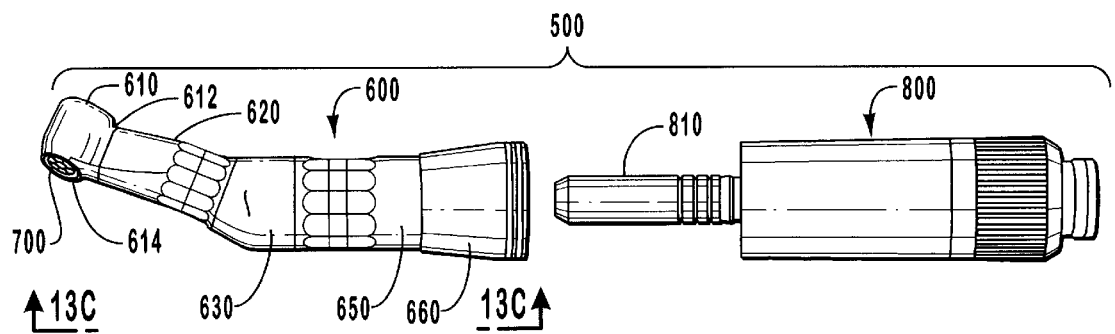
FIG. 13A is a perspective view of an endodontic handpiece including the head and the motor.
Figure 13B:
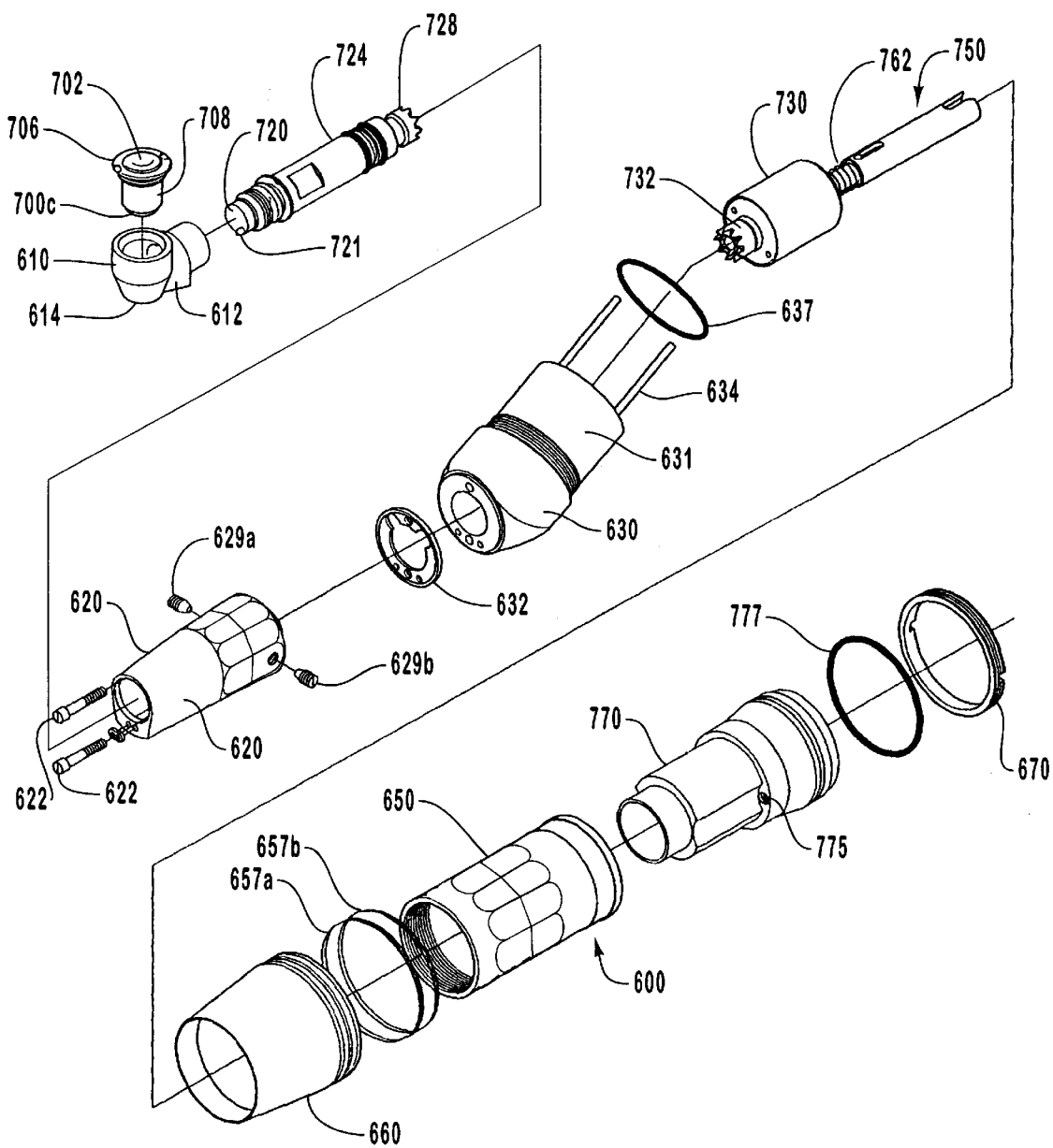
FIG. 13B is an exploded perspective view of the endodontic handpiece head shown in FIGS. 11A–11E and in FIG. 13A.
Figure 13C:
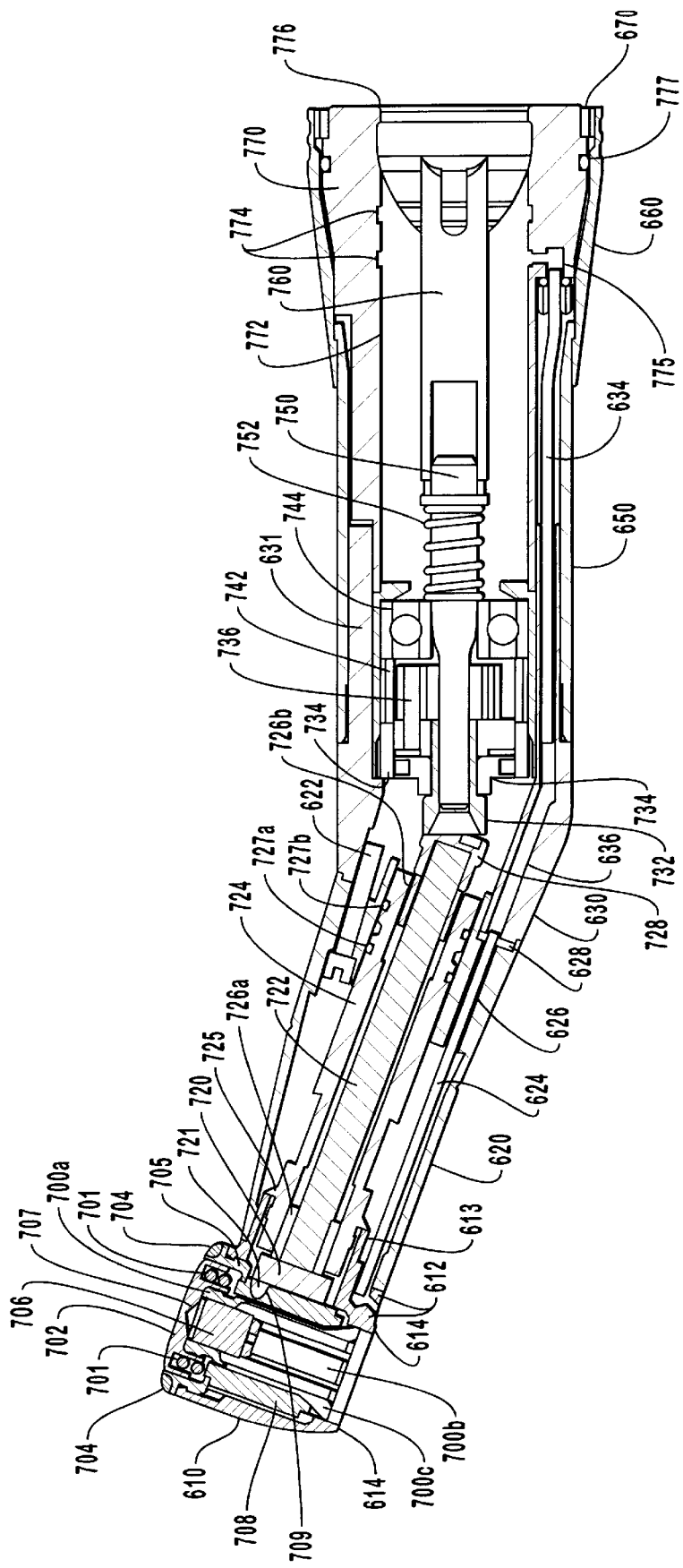
FIG. 13C is a cross-sectional view of the endodontic handpiece head shown in FIGS. 11A–11E and in FIGS. 13A–B.

FIGS. 11–13 depict a dental handpiece 500 used to couple with instruments such as those shown at 100, 200, 300 and 400. FIGS. 11A–11E depict the use of handpiece 500 and its primary features in relation to the use of endodontic instruments having handles configured to vary the working length of the instrument. FIG. 12 depicts an alternative embodiment. FIGS. 13A–13C depict in detail the elements of handpiece 500, particularly head 600 while the other component of handpiece 500, motor 800, is shown only in FIG. 13A as essentially any conventional motor may be coupled with head 600.

FIG. 11A–11B depict instrument 100 being held by chuck 700 as handpiece at 500 is used to clean a tooth 90. Head 600 has a head element 610 which holds chuck 700. Head element also has a neck extension 612 which is coupled to neck element 620. Note that rim 614 of head element 610 is essentially coplanar with any bottom surfaces of head element 610. More particularly, rim 614 is essentially coplanar with the bottom surface of neck extension 612 and neck element 620. This essentially coplanar configuration is particularly useful since rim 614 is used as a stop as it is rested on the coronal surface of tooth 90.

The ability to use rim 614 as a stop is significant advantage over conventional handpieces as it eliminates the need for rubber stoppers. Since rim 614 is immovable, use of the present invention provides a practioner assurance that once the working length of the instrument is set there will be a secure stopping action to prevent insertion beyond the desired length and it will not change due to movement of a stop. The practioner can also be assured that the working length of the instrument, the portion extending from chuck 700 beyond rim 614, is securely set once handle 110 is positioned in chuck 700.

Figures 1, 2:
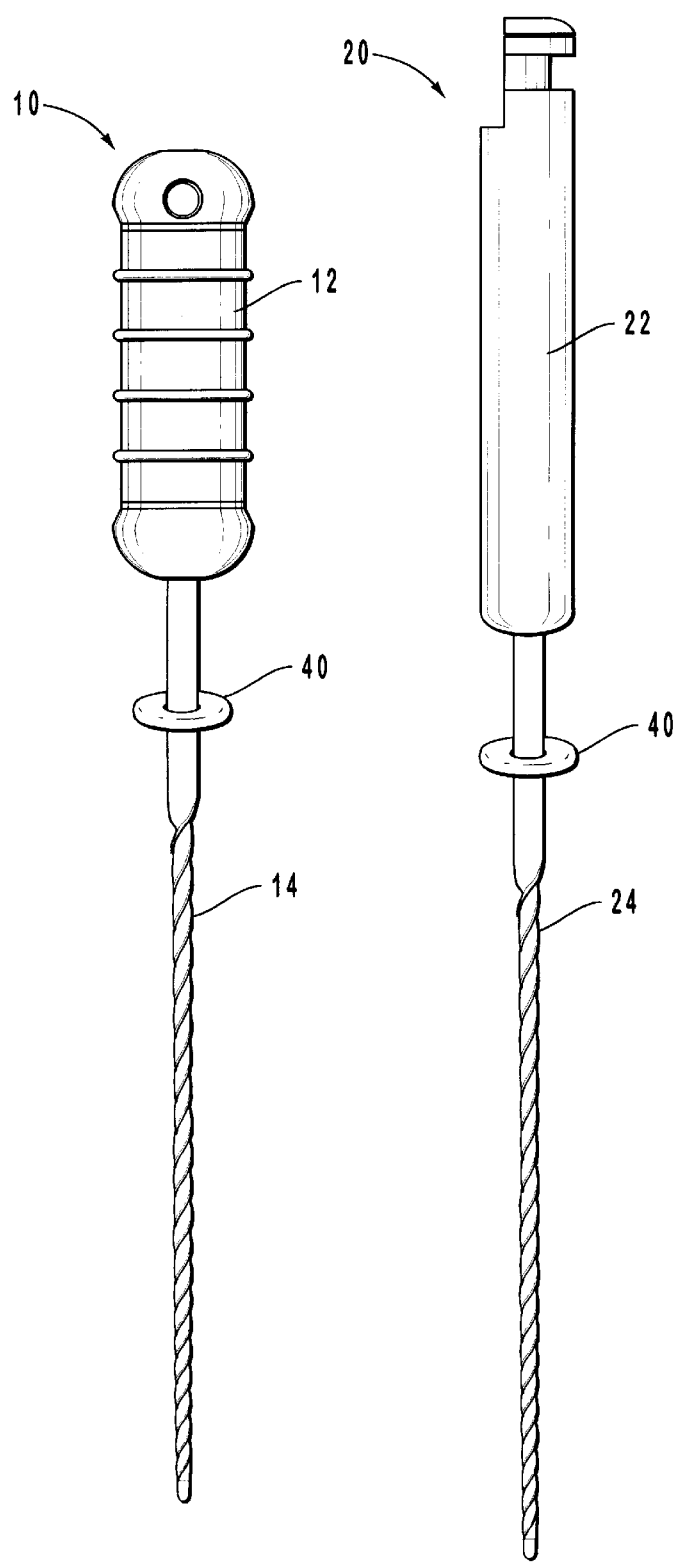
FIG. 1 is a perspective view of an instrument having a prior art peanut-shaped handle.
FIG. 2 is a perspective view of another instrument having a prior art latch-type handle.
Figure 3:
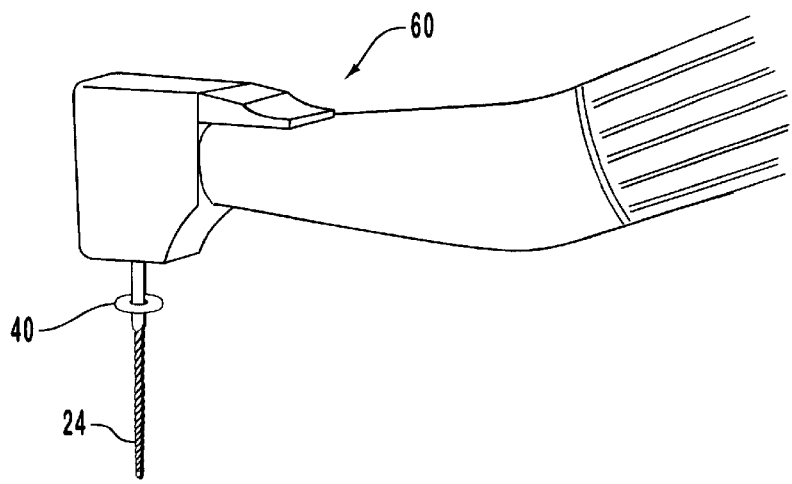
FIG. 3 is a perspective view of a head of an endodontic handpiece holding the instrument shown in FIG. 2.
Figure 4:
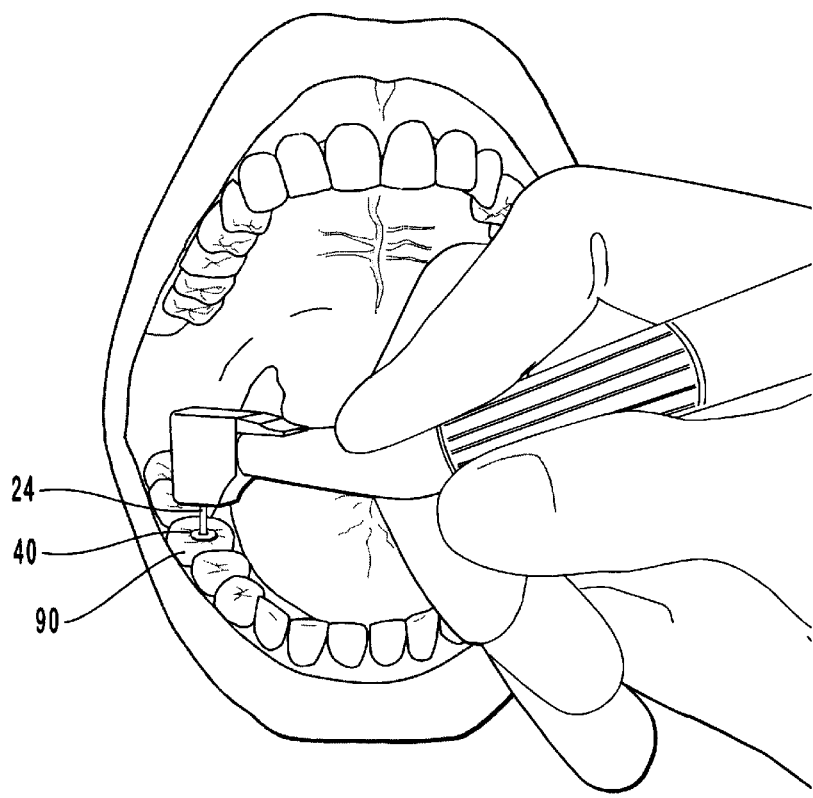
FIG. 4 is a perspective view of the endodontic handpiece shown in FIG. 3 being used in an endodontic procedure.

The essentially coplanar configuration enables a practioner to easily identify the position of rim 614 relative to the coronal surface of the tooth since it is at least essentially the same as that of the larger neck element 620. Another advantage of this configuration is the reduced size of head element 610. While rim 614 can also be fully coplanar with neck extension 612 and neck element 620, there is preferably a slight differential or offset, such as 0.1 mm or 0.2 mm, as shown. Additionally, a head may be used which has a conventional configuration such as is shown in FIG. 4 wherein the rim and the neck element have a more significant offset.

As described in detail in reference to FIGS. 11C–11E, handle 110 is firmly held by chuck 700 at variable positions which is preferably activated by a push button chuck mechanism. FIG. 11C depicts chuck 700 in an open position ready to receive handle 110 of instrument 100 while FIG. 11D depicts chuck 700 in a closed or engaged position securely holding handle 10. Chuck 700 is moved into an open position by pressing cap or push-button 702 and into a closed position as shown in FIG. 11D by releasing cap 702.

Note in FIG. 11C that pressing cap 702 causes chuck 700 to be depressed towards rim 614 and retention arms 700b of chuck 700 to be expanded. After handle 110 is positioned within chuck 700 and cap 702 is released, retention arms 700b of chuck 700 clamp around handle 110. The interface between retention arms 700b of chuck 700 and handle 110 is more clearly seen in FIG. 11E which is an exploded perspective view of only instrument 100, chuck 700 and head element 610.

As shown in FIG. 11E, the diameter and the cross-sectional shape of the gripping sections of handle 110 are the same. Since identification band 120 is sufficiently thick to fill band groove 118 such that the surface of identification band 120 is level with the gripping sections, the only sections of handle 110 which are not essentially the same between top end 111 and a bottom end 113 are bevelled section 114 and shallow recess 116. Note however, that handle 110 can still be held firmly within chuck 700 when shallow recess 116 extends out of chuck 700 due to the length of the remainder of handle 110 in chuck 700. This is possible since bevelled section 114 and shallow recess 116 are both located at top end of handle 110 and are only a small portion of handle 110. Note that chuck 700 can even hold handle 110 in a secure manner such that instrument 100 rotates concentrically when only top gripping section 119 is in chuck 700. However, instrument 100 is not intended to be used for such large length variations as it is then necessary to measure the working length. Instrument 100 is preferably used for small variations in length, 1 mm to 3 mm, by extending only the sections at top end 111 of handle 110 out of chuck 700 which have 1 mm incremental lengths.

FIG. 11E also shows that once retention arms 700b of chuck 700 clamp onto handle 110, arms 700b are in an essentially parallel configuration with handle 110. The primarily uniform shape of handle 110, or the uniform shape of the surfaces of handle 110 contacted by arms 700b, and the parallel configuration of arms 700b when in the engaged position enables handle 110 to be firmly held with varying portions of handle 110 in chuck 700. More particularly, handle 110 is held by pressure exerted by retention arms as the flat sidewall surfaces of handle 110 are contacted by or mated with the correspondingly flat retention arms 700b. The latchless configuration of the handles disclosed herein is in contrast to prior art handles such as handle 22 which require the use of a latch in the chuck to hold and rotate the handle.

Chuck 700 can also similarly hold handle 210 of instrument 200 as handle 210 has a diameter and cross-sectional shape which is essentially the same along its entire length from top end 211 to bottom end 213. The shape of handle 210 combined with the series of gradient markings 216 formed thereon enable handle 210 to be used to make relatively large variations in the working length of instrument 200 and to still be able to identify the working length without measuring it.

FIG. 12 is an exploded perspective view like FIG. 11E which depicts retention arms 700b' of chuck 700' holding handle 410 of instrument 400. As shown in FIG. 12, retention arms 700b' are configured to mate with ridges 416 of handle 410. This mating configuration ensures that the working length is adjusted in discrete increments such as 1 mm. Handle 410 can also be held in a chuck such as chuck 700 shown in FIGS. 11A–11E as the ridges provide sufficient surface area to engage with retention arms 700b in a secure manner. Similarly, handle 310 can be held in a chuck (not shown) having rounded extensions configured to extend into grooves 316 in a mated configurations or by a chuck such as chuck 700 as gripping sections 312 provide a large surface area for engagement with retention arms 700b. In summary, whether the handle has pointed ridges as shown in FIG. 12, sloped ridges, curved grooves, perpendicular recesses which partially encircle or fully encircle the handle, the retention arms can be flat or have a shape which corresponds with that of the handle in a mated configuration. It is however, preferable for the retention arms to grip the handle in a configuration such that the majority of the surface of the sidewall of the handle is in contact with the retention arms. Stated otherwise, the gripping sections of the handle are preferably at least half of the surface area of the handle other than its top and bottom surfaces.

Reference is now made to FIGS. 13A–13C to describe in detail the elements of head 600. FIG. 13A shows the exterior of the elements of head 600 as assembled and also motor 800. FIG. 13B is an exploded perspective view and FIG. 13C is a longitudinal cross-sectional view taken along cutting line 13C—13C of FIG. 13A.

Chuck 700 is shown having retention arms 700b which integrally extend from cylindrical portion 700a with spaces between each retention arm 700b. Alternatively, the retention arms can also be individual components which are not part of an integral cylindrical portion. In any event, the retention arms are configured to receive the handle of an endodontic instrument and to be pressed against the handle in a mated configuration such that the handle is firmly and concentrically held in varying positions relative to the chuck in order to vary the working length of the instrument, preferably by set increments. Chuck 700 and 700' are examples of chuck means for receiving and then releasably holding a handle.

A chuck spring 701 is positioned under cap 702 such that cap 702 is spring biased and pressure must be applied to depress cap 702. Cap ring 704 is positioned around cap 702. Depression of cap 702 enables the interior side of cap 702 to be urged against cylindrical portion 700a of chuck 700 and also against plug 706, via plate 707 on plug 706, which are located within cylindrical portion 700a. Sleeve 708 prevents cap 702 from being further than is needed. Chuck spring 701 and cap 702 are an example of means for actuating the chuck such that the handle of an instrument may be received and released by the chuck.

Retention arms 700b of chuck 700 are slightly compressed together within chuck sleeve 708 such that they expand outward as shown in FIG. 11C when depressed as result of cap 702 being pushed. When cap 702 is released, spring 701 pulls chuck 700 upward such that flange portions 700c of retention arms 700b are moved away from rim 614 back inside head element 610 toward sleeve 708. Head element 610 is an example of a head element means for containing the chuck.

Chuck sleeve 708 has a movement receptacle 709 which is a depression configured to receive eccentric protuberance 721 of cam 720. Cam 720 reciprocates and transfers the reciprocating motion to chuck sleeve 708 and chuck 700 via the coupling of protuberance 721 in receptacle 709. The reciprocating motion of cam 720 therefore enables an instrument held in chuck 700 to be rotated in a reciprocating manner. The range of motion being about 30°. The combination of receptacle 709 in chuck sleeve 708 and protuberance 721 of cam 720 provides an examples of means for rotating the chuck. The chuck rotating means may also include the other components as described herein which rotate cam 720 such as cam shaft 722 and other connected components. Neck element 620 is an example of housing means for supporting the chuck rotating means. The housing means may include other external elements of head 600 as described hereinbelow which house or support the chuck rotating means such as elbow element 630, sheath element 650, and cone sleeve element 660 as well as a component which is primarily an internal component such as ferrule 770.

As noted above, cam 720 is coupled to cam shaft 722. Cam shaft extends within bearing sheath 724. A gear 728 is located on cam shaft 722 opposite cam 720. Cam 720 and gear 728 extend beyond bearing sheath 724 such that cam shaft 722 is only shown in the cross-sectional view of FIG. 13C. Bearing sheath 724 has a flange 725 which extends radially outward and is positioned in contact with sheath engagement portion 613 of neck extension 612. Cam shaft 722 rotates against bearings 726a and 726b which are located at the opposing ends of cam shaft 722. O-rings 727a and 727b are positioned around bearing sheath 724.

Neck element 620 is coupled to elbow element 630 by a screw 622. A member 624 extends within the chamber defined by neck element 620 and into a channel 626. Elbow element 630 also has a channel 636 which is aligned with channel 626. A pin 628 is positioned through member 624 at the juncture of channel 626 and channel 636 such that member 624 barely extends into channel 636 as shown in FIG. 13C. Screws 629a and 629b also extend into neck element 620. Sealing washer 632 shown in FIG. 13B is not shown in FIG. 13C.

Gear 728 engages gear 732 of planetary gear carrier 734. Planetary gear carrier 734 is shown in FIG. 13C but is hidden in FIG. 13B by bearing sheath 730. Planetary gear carrier 734 has a large gear 736 which is engaged by a ring gear identified in FIG. 13C at 742. Planetary gear 734 transmit rotation, at a ratio of 4:1, to ring gear 742.

As shown in FIG. 13C, a long face pinion 750 extends into planetary gear carrier 734 and rotates within ball bearing 744. As shown in FIG. 13B and FIG. 13C, the other end of pinion 750 extends into shaft 760 with a spring 752 positioned to be compressed between ball bearing 744 and shaft 760.

Shaft 760 extends within a receiving chamber 662 defined by ferrule 770. Chamber 772 has slots 774 and an opening 776. Chamber 772 and opening 776 are configured to receive drive shaft 810 of motor 800 which is configured to engage shaft 760.

Elbow element 630 has a sheath portion 631 which is coupled within sheath element 650. Note that members 634 extend from channel 636 of elbow element 630 and are engaged by receptacle 775 of ferrule 770.

Cone sleeve element 660 fits over sheath element 650 in an interlocking manner as shown in FIG. 13C. Cone sleeve element 660 also fits over ferrule 770. Positioned between cone sleeve element 660 and ferrule 770 are o-ring 777 and threaded ring 670. Note that o-rings 657a and 657b shown in FIG. 13B are not shown in FIG. 13C.

In addition to the endodontic handpiece head or contra-angle shown at 600 and as described above, other contra-angles may have similar features. Examples of suitable contra-angles include those sold by DynaDent as 24641, those sold by KaVo as 3LD or as 53LDN, those sold by Kerr as M4, those sold by Micromega as 6/15AE, those sold by MTI as LX-EF and those sold by NSK as TEP-E10R, TEQ-E10R, IS-35 and IS-40.

Examples of patents which disclose various designs for chucks include U.S. Pat. No. 3,646,677 entitled Collet Chuck for a Dental Instrument; U.S. Pat. No. 4,536,157 entitled Lever Actuated Chuck Mechanism for Dental Handpiece; U.S. Pat. No. 4,595,363 entitled Dental Handpiece Having Means for Opening and Closing a Chuck; U.S. Pat. No. 4,611,990 entitled Dental Handpiece Construction; U.S. Pat. No. 4,661,062 entitled Dental Handpiece Contra-Angle Head; U.S. Pat. No. 4,874,314 entitled Socket to Clampingly Hold Dental Tools; U.S. Pat. No. 5,090,906 entitled Push-Button Control Device for a Dental Instrument and European Patent No. D 281 847 B1. These patents are all incorporated by reference.

In addition to the above patents the following patents which are owned by NSK of Japan are also incorporated by reference. These patents include: U.S. Pat. No. 5,857,851 entitled Dental Handpiece; U.S. Pat. No. 5,807,108 entitled Dental Handpiece; U.S. Pat. No. 5,718,582 entitled Dental Tool Chuck; U.S. Pat. No. 5,688,122 entitled Chucking Device for a Dental Tool; U.S. Pat. No. 5,575,648 entitled Dental Turbine Spindle Assembly; U.S. Pat. No. 5,567,154 entitled Dental Turbine Drive Having Means for Automatic Speed Control; U.S. Pat. No. 5,476,380 entitled Dental Handpiece; U.S. Pat. No. 5,425,638 entitled Turbine for a Dental Handpiece; U.S. Pat. No. 5,423,678 entitled Handpiece Having Bearing Protective Member; U.S. Pat. No. 5,340,311 entitled Dental Handpiece; U.S. Pat. No. 5,312,252 entitled Turbine for a Dental Handpiece; U.S. Pat. No. 5,275,558 entitled Dental Handpiece, Bur Mount Operating System; U.S. Pat. No. 5,057,015 entitled Dental Handpiece Having an Arrangement to Form Compatible Connections to Differently Designed Rotatable Joints; U.S. Pat. No. 5,040,980 entitled Dental Handpiece With Spring Grip Chuck and Lever Release Mechanism; U.S. Pat. No. 4,973,247 entitled Dental Handpiece Assembly; U.S. Pat. No. 4,921,424 entitled Dental Handpiece; U.S. Pat. No. 4,786,251 entitled Dental Handpiece and High Speed Turbine Assembly; U.S. Pat. No. 4,690,641 entitled Contra-angle or Turbine Head of a Dental Handpiece; U.S. Pat. No. 4,642,051 entitled Dental Handpiece; and U.S. Pat. No. 4,595,363 entitled Dental Handpiece Having Means for Opening and Closing a Chuck.

The endodontic instruments disclosed herein as having a handle configured within the scope of the present invention can have any suitable file. While conventional files may be utilized and the instruments may be utilized in accordance with conventional methodologies, the instruments preferably have files which are specifically adapted for cleaning the upper portions of a root canal without cleaning the apical portion. Such instruments and related methods are disclosed in U.S. Pat. No. 6,012,921 which is entitled "Endodontic Systems for the Anatomical, Sectional and Progressive Corono-Apical Preparation of Root Canals with Three Sets of Dedicated Instruments. U.S. Pat. No. 6,012,921 is a continuation-in-part of U.S. Pat. No. 6,045,363 entitled Endodontic Methods for Progressively, Sectionally and Anatomically Preparing Root Canals with Specific Instruments for each Section having Predetermined Working Lengths. These patents claim priority through two U.S. patents issued to Francesco Riitano including U.S. Pat. No, 5,775,904 and U.S. Pat. No. 5,642,998 which are both entitled Endodontic Instrument for Rapid Widening of the Canal Mouth and Specific Rectification of the First Two-Thirds to Italian Patent Application. All of these patents are issued to Francesco Riitano and are owned by Ultradent Products Inc. of South Jordan, Utah. No. RM95A000377 which was filed on Jun. 6, 1995. For purposes of disclosure of the present invention, each of the foregoing applications and patents is incorporated herein by specific reference.

The systems and methods of endodontic instruments disclosed in essentially involve sequentially cleaning a root canal in sections from the crown to the apex by dividing it into three sections including an operative coronal portion, an operative middle portion and an apical portion. An operative phase generally corresponds with the particular sections or portions of the operative root canal and specific instrumentation is used in each phase. An overview of the methodology is provided hereinbelow; however, the cleaning of the root canal up to the apical portion is the phase which is most related to the present invention.

Figure 14A:
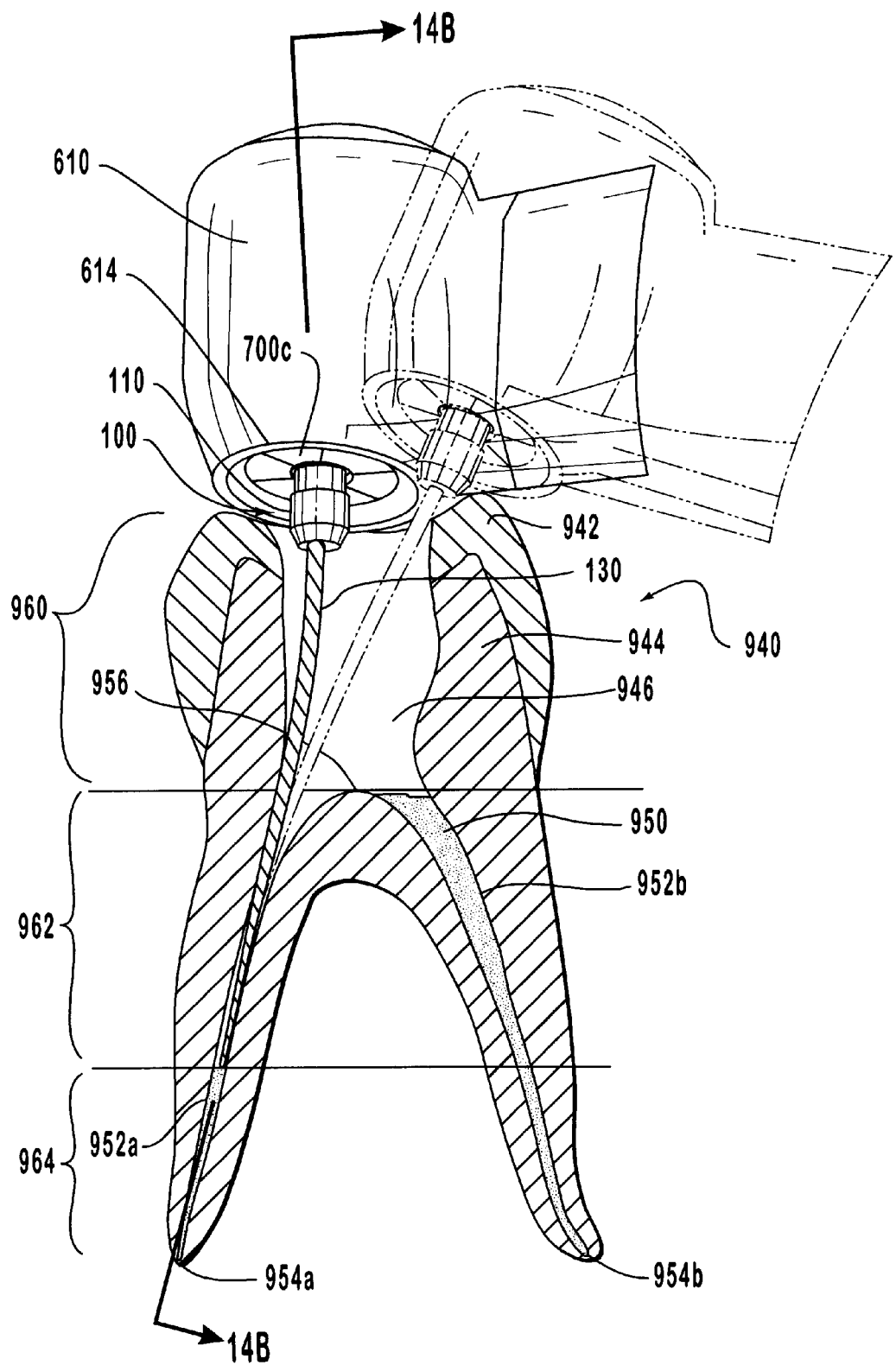
FIG. 14A is a longitudinal cross-sectional view of a tooth with a file portion of a file instrument inserted into the root canal up to the apical portion.

Before describing the methodology, it is necessary to set forth the divisions of the operative root canal as shown in FIG. 14A. During root canal therapy, the operative root canal is considered to include the anatomical root canal, which extends from the pulp chamber or the floor 956 of the pulp chamber 946 to the apex 954, and the operative coronal portion 960 thereabove. More specifically, the operative root canal comprises the operative coronal portion 960, the operative middle portion 962 and the apical portion 964. Operative coronal portion 960 essentially includes the access cavity walls. The operative middle portion 962 is the upper portion of the anatomical root canal while the apical portion 964 is the lower portion of the anatomical root canal.

The divisions of the operative root canal are distinguished from the nomenclature of the anatomical root canal as used to designate the sections before opening the tooth wherein the anatomical root canal is divided into the apical portion and the coronal portion. The coronal portion of the anatomical root portion is conventionally defined as the upper portion of the anatomical root canal which terminates at the floor of the pulp chamber. However, once the pulp chamber is exposed and instruments are introduced into the root canal, the opening into the tooth should be treated as an extension of the operative root canal as it is then a continuous chamber or open tract. Accordingly, the access walls are considered part of the operative root canal and are designated as the operative coronal portion or the access portion.

Apical portion 964 extends from the apex of root canal 952 up to an area of anatomical root canal 952, such that the length of the apical portion is less than half of the length of the anatomical root canal as measured from the apex to floor 956. Apical portion 964 is accordingly generally the bottom one-half to one-third of the anatomical root canal 952. The actual length of the apical portion varies depending on many factors such as the type of tooth and the age of the tooth. However, the apical portion typically has a length in a range from about 3 mm to about 4 mm as measured from the apex.

As also indicated hereinabove, operative middle portion 962 is the top portion of the anatomical root canal 952 and extends from floor 956 down to an area of anatomical root canal 952, such that the length of the operative middle portion is greater than half of the length of anatomical root canal 952. More specifically, operative middle portion 962 is generally the top two-thirds of anatomical root canal 952 as measured down from floor 956. The length of operative middle portion can be estimated by identifying the overall length of the root canal, typically by use of radiography, and then subtracting about 3 mm to about 4 mm from the overall length.

As previously indicated, the three sections are treated in primarily distinct sequential phases. These phases include: preparation of the operative coronal portion, cleaning or preparation of the operative middle portion, and finally cleaning of the apical portion. Additionally, access into the apical root portion is preferably improved before the apical portion is cleaned.

FIG. 14A depicts the upper portions of root canal 952*a* of tooth 940 being cleaned with instrument 100 after several steps in the methodology have been achieved as described hereinbelow. The first phase or coronal phase involves exposing the pulp chamber and also preferably other steps to enhance accessibility into operative middle portion 962 and also apical portion 964. Accordingly, the coronal or access phase is initiated by exposing pulp chamber 946 through removing the top of the chamber. More particularly, the overhanging portions of enamel 942 and dentin 944 are first removed. Once pulp chamber 946 has been exposed, the pulp material 950 contained therein is removed. At this point, pulp material 950 still extends within root canal 952 from apices 954*a* and 954*b* to the floor 956 of pulp chamber 946.

After an opening is formed into the tooth to provide access into the root canal during the first phase, it is preferable to remove or reduce dentinal or enamel protrusion or irregularities that may obscure or hinder access of instruments into the remaining portions of the operative root canal. For example, dentinal shelves as shown at 966 depicted in FIG. 14A are preferably reduced or rectified to provide greater access for instrumentation during the subsequent phases. More particularly, interferences are preferably removed or minimized such that instruments can be inserted in the anatomical root canal in a relatively straight manner. Accordingly, FIG. 14A depicts file 130 inserted into root canal 952*a* with the dentinal shelf removed thereabove and as not being yet removed above the other canal, 952*b*. Rectification or regularization can be achieved by any suitable means. An example of a means for rectifying dentinal shelves is set forth in U.S. Pat. No. 5,642,998 which was incorporated by reference hereinabove. It may also be necessary to widen the tract of the operative coronal root canal.

Once the operative coronal portion has been adequately prepared, it is preferable to prepare an x-ray image of the tooth to identify the length of the operative root canal in order to determine the preferred working length for the instrument or set of instruments to be used in the next phase. The preferred working length is preferably identified by subtracting about 3 mm from the total radiographic length of the operative root canal. The total radiographic length is preferably derived from a radiograph made using a localizator and a long cone radiographic head.

The second phase involves cleaning or preparation of operative middle portion 962. It may also involve to some extent further rectification of the operative coronal or access portion 960 through further removal of any ledges or outcroppings which prevent straight and easy access into the operative middle portion 962. Additionally, it may also involve some degree of rectification of the upper region of operative middle portion 962.

The length of each file in the set used to clean the operative middle portion depends on the length of the tooth being cleaned. More particularly, after identifying the length of the root canal from an x-ray image, the length of the file to be used in the operative middle portion is determined by subtracting 3 mm from this identified length of the root canal. This length is typically between about 15 and about 20 mm, however, longer files, such as a 25 mm long file, are typically required for canine teeth. To provide for the different root canal configurations which may be encountered, it is preferred to have files with lengths ranging from about 8 mm to about 35 mm. However, files with lengths ranging from about 10 mm to about 30 mm will be most utilized and files with lengths ranging from about 14 mm to about 26 mm will be the most frequently utilized.

After identifying the combined length of the operative middle portion and the operative coronal portion and after removing the overhanging enamel 942 and dentin 944, the practitioner selects an instrument or a set of instruments with a file length which approximately corresponds with the combined length of the operative middle portion length and the operative coronal portion. Handle 110 of instrument 100 is then positioned within chuck 700 and is locked into place once the position of handle 110 relative to chuck 700 is such that the working length of instrument 100 corresponds with the combined length of the operative middle portion and the operative coronal portion of the root canal. Handpiece 500 can then be used to rotate instrument 100 as shown. As indicated above, instrument 100 is preferably rotated in a reciprocating motion such that instrument 100 rotates for example, clockwise for half of a revolution and then counterclockwise for half a revolution. A reciprocating motion is preferred as such motion enables the file to alternately engage material 950 and the walls of the operative middle portion of the root canal in a manner that removes material 950 and to then rotate in the opposite direction such that the file 130 less aggressively engages material 950 and the operative middle portion walls, depending on the file design. Accordingly, rotating instrument 100 in a reciprocating motion minimizes breakage of file 130 when file 130 encounters a surface that prevents rotation of instrument 100 in a direction that enables cleaning and removal of material 950. Instrument 100 may, however, also be continuously rotated in one direction only or be vibrated.

As shown in FIG. 14A, file 130 is inserted into root canal 952*a* down through operative middle portion 962 without extending substantially into apical portion 964. By limiting the working length of instrument 100 such that it cannot significantly extend into apical portion 964 once positioned in chuck 700, a practitioner can aggressively clean the operative middle portion without worrying that the instrument will overly thin the root canal, perforate the apex or that cleaning will cause extrusion of material through the apex. Another benefit of cleaning the operative middle portion first is that the apical portion is then generally more accessible and easily cleaned. Additionally, since instruments are selected for use in cleaning the operative middle portion which have files lengths that do not permit entry into the apical portion once properly positioned within a chuck of a handpiece such as handpiece 500, the likelihood of jamming or breaking a tip of an instrument while working in the confined space of the apical portion is prevented.

Figure 14B:
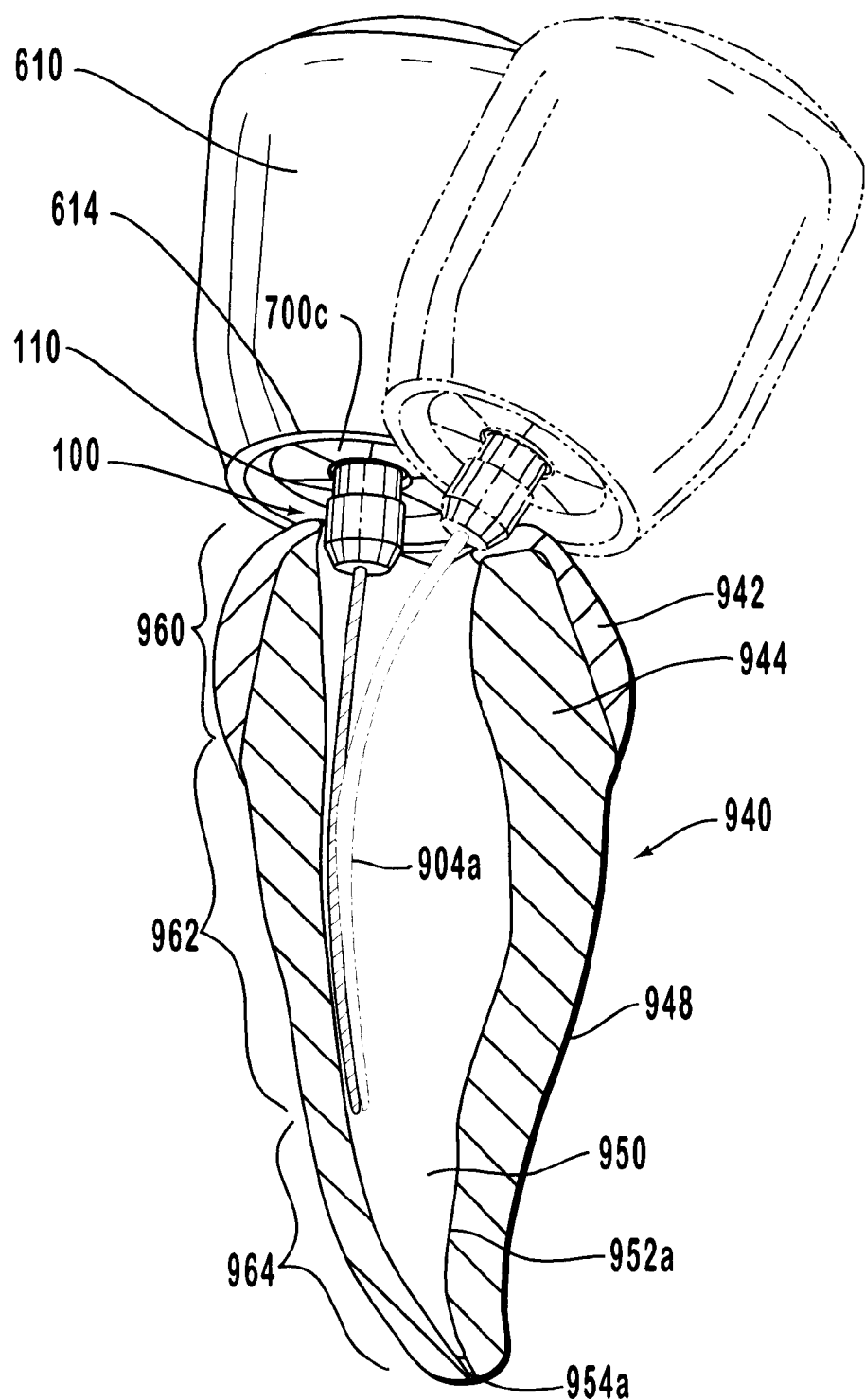
FIG. 14B is a longitudinal cross-sectional view of the tooth shown in FIG. 14A taken along cutting line 14B—14B to depict the cleaning of the pulp material from the operative middle portion of the root canal.

By instrumenting in the operative middle portion and the operative coronal portion before the cleaning the apical portion, the practitioner can use an instrument that is relatively flexible compared to the conventional instruments. As shown in FIG. 14B, which is a cross-sectional view taken along cutting line 14B—14B of tooth 940 in FIG. 14A, file 130 is sufficiently flexible to be flexed or curved against any surface of operative middle portion 962 or operative coronal portion 960 and yet is sufficiently rigid to remain flexed against the surface during a cleaning motion such as a longitudinal motion, a rotational motion or a reciprocating rotational motion. The file is also sufficiently resilient that substantial deformation of the file does not occur due to the forces experienced during cleaning of the pulp material from the root canal. The files are designed to have such flexibility and rigidity by properly selecting a combination of factors including the diameters of the files at the proximal or top ends and at the tips as well as the material used to form the files.

Instrument 100 is shown in FIGS. 14A and 14B being moved in a longitudinal movement or up and down movement as well as being rotated while file 130 is flexed or arched to urge the file against the root canal surfaces. As shown, the configuration of the files used to clean the operative middle portion, and preferably the operative coronal portion as well, enable a practitioner to move the files around the perimeter or from side to side to contact the perimeter. More particularly, the files are pushed against the surfaces of the root canal and simultaneously moved around the perimeter or periphery of the root canal until the practitioner has reached the beginning location of the cleaning and shaping process.

Since the file is moved around the perimeter, the file has more than one center of motion during cleaning of the operative middle portion of the root canal, such as a pivot point or center of rotation, as the tip of the file or at least a part of the abrading portion does not generally remain primarily in one position. This is in sharp contrast to prior art methods which limited the practitioner to essentially rotating a conically shaped file to yield a cone shaped borehole. Such prior art methods yield a final anatomy that is dictated by the shape of the instrument. More particularly, prior art methods result in an anatomy with a significant footprint from the instrument, which is a borehole that obviously corresponds to the shape of the file, without even cleaning all of the perimeter of the root canal. In addition to failing to fully clean the root canal, the tooth can be overly thinned, perforations may result or the tooth may be unnecessarily weakened when cleaned by such prior art methods.

The contours of the operative coronal portion and the operative middle portion can be used during their cleaning by a practitioner as a guide for the movements of the files due to the properties of the files such as flexibility, rigidity and limited working length. As a result of the ability to move the file by following the contours of the operative middle portion during cleaning and shaping, the original anatomy of the root canal is substantially maintained despite the cleaning of essentially all pulp material from the operative middle portion. For example, when the original perimeter is, generally elliptical, the files can be urged along one side and then along the next side wall in a manner such that the resulting cleaned and shaped root canal has a perimeter that is still generally elliptical. Similarly, if the original shape of the perimeter of a root canal as seen from a transverse cross-sectional view, is generally circular, laminar or tear shaped, then the cleaned and shaped walls will also be generally circular or tear shaped. In other words, the original anatomy of the root-canal controls the shape of the resulting cleaned and shaped anatomy due to this methodology. The understanding that the final anatomy is guided by the shape of the original anatomy enables a practitioner to more confidently urge a file such as file 130 against all surfaces of a root canal and aggressively clean all of the surfaces of the operative middle portion of the root canal since the likelihood of overly thinning the root canal or causing lateral perforations is diminished.

As indicated above, the ability of instruments having such files to clean the operative middle portion of a root canal is enhanced when the instruments also have handles configured for incremental adjustment and are used in combination with an appropriate handpiece. Benefits are described in detail hereinbelow of using such instruments together with a handpiece which has a chuck configured to hold an incrementally adjustable handle in a mated configuration and a rim around the chuck.

One of these benefits is the secure stopping action provided by a rim such as rim 614. As set forth above, rim 614 is not movable so the practioner is assured that once the working length of the instrument is set there will be a secure stopping action to prevent insertion beyond the desired length and it will not change due to movement as may occur with conventional stoppers such as stopper 40. While such a rim is useful with conventional root canal therapy techniques, it is particularly useful for cleaning the operative middle portion in the systems and methodology described above. Conventional endodontic techniques generally involve the mere rotation of a set of instruments of increasing size in one location. Such motion presents less opportunities for a stopper to be dislodged when compared with cleaning the operative middle portion by following the contours of the root canal while flexing the file against the root canal surfaces. More particularly, the cleaning movements required to follow root canal contours while flexing the instrument is much more aggressively oriented than conventional techniques so the secure stopping action provided by rim 614 enhances the ability to use such a methodology as a practioner is assured of the safety of the methodology. Note that although the movements may be more aggressive, the results of the methodology are much less aggressive in terms of the removal of dentin compared with conventional techniques.

Many practioners use several standard length instruments such as those having a length of 21 mm or 25 mm and then adjust the length through the use of stoppers. Some practioners, however, prefer to avoid the use of rubber stoppers by using endodontic systems with sets of instruments having as many different lengths as are needed to clean root canals by conventional techniques. For example, a system may be sold wherein instruments have incrementally different lengths such as 21 mm, 22 mm, 23 mm, 24 mm and 25 mm, thereby eliminating the need for stoppers in this range. Due to the aggressive movements involved in cleaning the operative middle portion, as described above, without the use of instruments having handles adapted for incremental adjustment and a corresponding handpiece head, some practioners might be more inclined to rely on a system of such instruments having incrementally different lengths. However, as the above discussion indicates, such a need is eliminated through the use of instruments having handles configured for incremental adjustment. Accordingly, since the working length of the instrument is adjustable by adjusting its position within a mated chuck by 1–3 mm or more less instruments are required to have a complete system. A practioner can confidently expect to clean all operative middle portions of root canals, in accordance with the methodology discussed above, with only a limited system of endodontic instruments or sets of instruments. This is an additional benefit of the use of instruments having handles adapted for incremental adjustment and having filed configured for cleaning the operative middle portion of a root canal in combination with an endodontic handpiece head having a chuck which mates with the handle.

It should be noted that when used to clean the operative middle portion in accordance with the methodology disclosed herein, the files are preferably configured to abrade along their entire length or nearly their entire length. An advantage of having nearly all or all of the portion of a file extending from a handle configured for abrading is that the file can simultaneously abrade both operative coronal portion 960 and operative middle portion 962. A primary benefit of simultaneously abrading both portions is the ability to further straighten the operative coronal portion while cleaning the operative middle portion. Accordingly, when it is necessary to adjust the working length such that handle 110 extends significantly into pulp chamber 946, it is especially useful to have the file adapted for abrading along its entire length or close thereto as handle 110 cannot abrade.

In contrast to being adapted to abrade along their entire length or nearly their entire length, a file of a conventional instrument typically has a smooth shank portion at its proximal end and an abrading portion which extends therefrom to its distal insertion end. Such shank portions are often about one-third of the overall length of the portion of the file extending from the handle. ISO standardized files have abrading portions of up to 16 mm and the remainder of the file is a smooth shank portion. Such conventional files frequently fail to remove interferences extending from the access or root chamber above the anatomical root canal so the instruments must bend around the interferences, thereby further increasing the likelihood of wall perforations, overthinning and failing to clean significant portions of the canal. It especially increases the likelihood of iatrogenic modifications resulting from the tip of the file.

Removal of pulp material 950 from operative middle portion 962 removes the majority of bacteria in the pulp canal since the majority of bacteria in an infected root canal is typically located in the operative middle portion. Not only is the greatest volume of bacteria in the operative middle portion but it is also believed that the concentration is greater in the operative middle portion. Since a certain minimum threshold must generally be reached for complications to arise due to microbial presence in a root canal, removal of the pulp material in the operative middle portion significantly reduces the likelihood of such complications.

By removing the majority of bacteria before cleaning the apical portion there is also less likelihood of exposing the surrounding tissue to bacteria due to overly thinning the root canal, perforation or extrusion of material from the canal. The greatest likelihood for the occurrence of complications such as over thinning of root canal walls, perforation or extrusion of material from the canal is in the apical portion. The apical portion is the most likely site for such complications as apical portions are more complex and delicate compared to the operative middle portions of teeth. Since such complications are most likely to occur in the apical portion, it is highly beneficial to have the material removed from the operative middle portion in order to minimize the amount of material that can come out of the root canal to cause problems. For example, in the event of an apical extrusion far less septic material may be expressed during instrumentation in accordance with present methodology than if the apical extrusion occurred as a result of cleaning in accordance with conventional methods wherein files are inserted to the apical portion before cleaning the operative middle portion. As a result, removal of the majority of bacteria before cleaning the apical portion increases the likelihood of successful root canal therapy in several ways compared with conventional methods.

Figure 15:
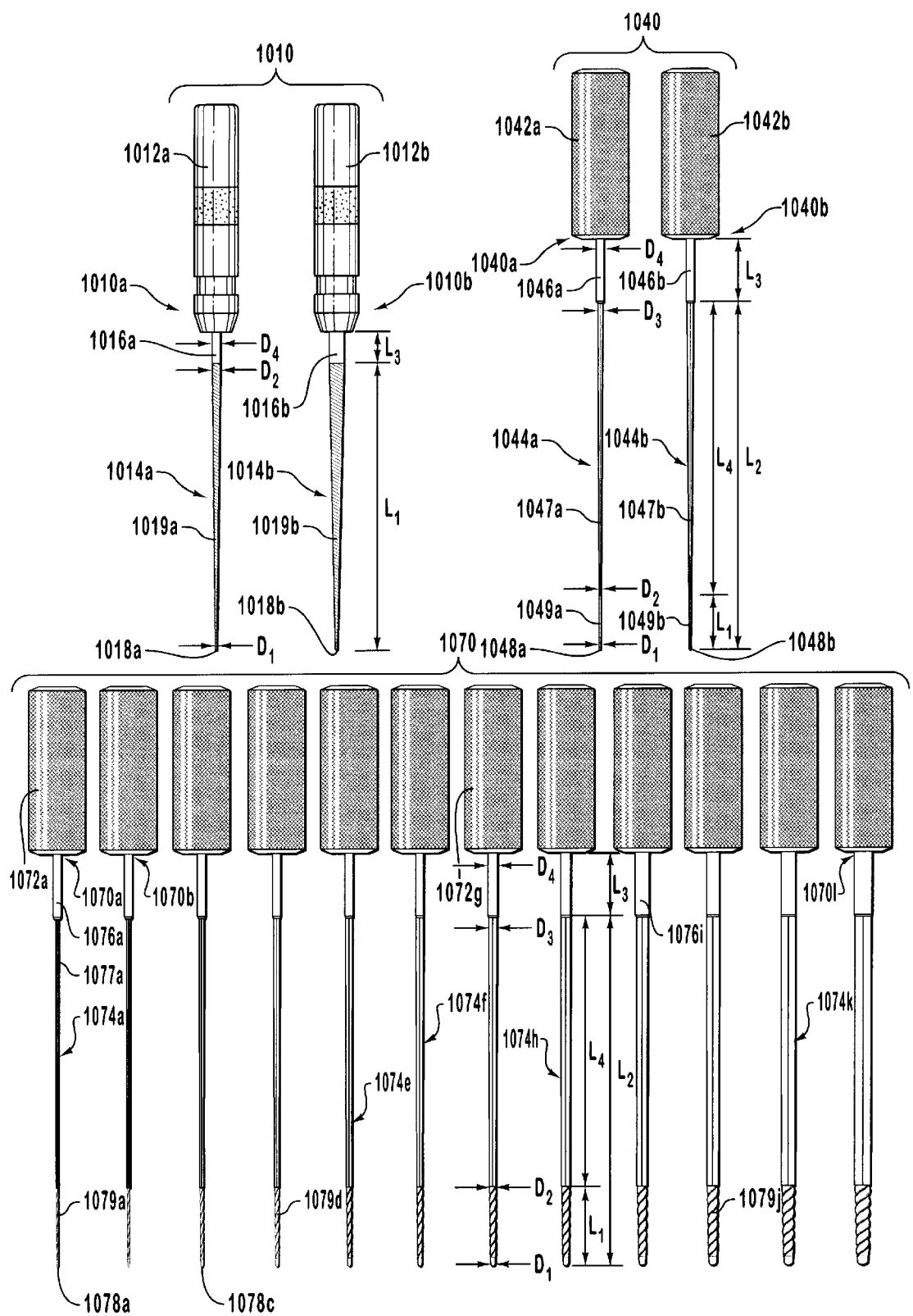
FIG. 15 is a view of a system of endodontic tools including a first set of instruments for cleaning the operative middle portion of an operative root canal, a second set of instruments for improving the access into the apical root portion and a third set of instruments for cleaning the apical root portion.

FIG. 15 depicts three sets of instruments identified at 1010, 1040 and 1070 which are used to prepare a root canal. The sets of instruments identified respectively at 1010, 1040 and 1070 are respectively used to clean the operative middle portion, to improve access into the apical portion and to clean the apical root portion. As shown, instruments 1010a and 1010b have files 1014a and 1014b. Each file has a shank portion 1016 which tapers to an abrading portion 1019 configured like conventional K-files and terminating at a tip 1018. Incrementally adjustable handles 1012a and 1012b are respectively positioned on smooth shank portions 1016a and 1016b. These handles are configured for use being held in a mated configuration by a chuck of a handpiece head. An instrument such as instrument 1010a or a set of instruments such as 1010a and 1010b comprises a first endodontic instrument means for anatomically removing and anatomically cleaning essentially all pulp material from the operative middle portion without significantly removing pulp material from the apical root portion.

As indicated above, the apical root portion of the root canal can be cleaned shown after removing and cleaning essentially all pulp material from the operative middle portion of an operative root canal in conformance with the anatomical shape of the operative middle portion by flexibly moving an instrument within the operative middle portion. However, it is preferable to improve the access into the apical root portion before cleaning the apical root portion of the root canal.

As shown in FIG. 5, the handles of the instruments used to improve the access into the apical root portion or to clean the apical root portion are not configured with an incrementally adjustable handle such as handles 1012a–b as these steps are preferably manually achieved. It is generally adequate to merely manually rotate the file within the apical root portion and/or move the file in a longitudinal motion. More specifically, after the file reaches the apex or approximately reaches the apex, the file is preferably moved upward while simultaneously being rotated, and it is withdrawn in order to be cleaned before being reintroduced. Although, the instruments used to improve the access into the apical portion or to clean the apical portion are not necessarily used with an incrementally adjustable handle in a handpiece, these steps are, however, briefly described herein to fully appreciate the systems and methodology.

It is beneficial to widen the tract of the root canal to provide access for thin irrigation needles into the apical root portion so as to maintain the smear layer in solution within the apical root portion, thereby avoiding smear layer accumulation. Additionally, it is useful to maintain the debris derived from cleaning the root canal in suspension to avoid filling the apical portion of the root canal with a plug. If the apical portion becomes filled, there is an increased likelihood that the progress of the instrumentation may be stopped or that debris may be pushed out of the tooth. Accordingly, by widening the access to enable irrigation needles to deliver irrigants to the apical root portion, the apical root portion is more accessible to the subsequent apical cleaning instruments and the cleaning instruments are less likely to be blocked.

Thin irrigation needles typically have a diameter no smaller than about 0.30 mm so it may be necessary to increase the diameter of portions of the root canal up to about 0.35 mm or even up to about 0.40 mm, particularly within the region of the boundary between the operative middle portion and the apical root portion. Note that the diameter need only be slightly larger than a thin irrigation needle in order to provide adequate access.

While the diameters of some root canals within the region of the boundary between the operative middle portion and the apical root portion and even within the apical portion may already be large enough to enable irrigation needles to deliver irrigants as far as is necessary, it is generally necessary to widen the diameter within the apical portions or at least at the tops of the apical portions. It is not necessary for the entire apical portion to be widened up to about 0.35 mm or about 0.40 mm; just enough of the apical portion should be widened so that the irrigants can be delivered as needed. However, the length of files used to widen the apical portion is preferably sufficient to at least approximately reach the apex. Accordingly, the top of the abrading portion may be flared to enable the upper area of the apical portion to be widened up to about 0.40 mm while the tip diameter which is at or near the apex is preferably significantly smaller. Note that in addition to abrading at least the top of the apical portion, it may also be necessary to widen the diameter at the region of the base of the operative middle portion with the widening at the top of the apical portion.

The files of instruments used to improve access into the apical portion and those used to clean the apical portion have similar configurations. Typically, the instruments used to improve the access into the apical portion, have the same lengths as the instruments subsequently used to clean the apical portion so that the entire apical portion is first widened and then cleaned. The lengths are preferably sufficient such that when the file is inserted into the root canal the tip can at least approximately reach the apex. Such file lengths are typically within a range from about 8 mm to about 35 mm, more typically in a range from about 14 mm to about 35 mm and most typically in a range from about 12 mm to about 33 mm.

The instruments, however, typically have different tip diameters and tapers along their respective abrading portions. The apical portion access instruments generally have much smaller tip diameters and much greater tapers than the instruments used to clean the apical portion for safe widening of apical portions. Note that before widening the apical portion of the root canal, it is preferable to make a predetermination of the desired diameter.

A file of an instrument designed for improving access to the apical root portion of a root canal or for cleaning the apical portion may be configured to abrade along its entire length; however, it preferably has an abrading portion from its tip part way upward towards its proximal end such that the remainder of the file is relatively smooth. More particularly, each file is preferably configured with an abrading portion along less than about half of the length of the file and more preferably about one-third of the length between its tip and top end. Accordingly, the length of the abrading portion is generally within a range from about 1 mm to about 35 mm, more preferably in a range from about 2 mm to about 16 mm and most preferably in a range from about 3 mm to about 6 mm. In a preferred configuration, the abrading portion is about 5 mm or about 6 mm.

FIG. 15 depicts set 1040, used to improve access into the apical portion, as including two instruments, 1040a–b. Each file has three sections including a smooth shank portion, a square portion and an abrading portion. For example, instrument 1040a has a file 1044a with smooth shank portion 1046a, a square portion 1047a, an abrading portion 1049a and a file tip 1048a. As shown, the smooth shank portion 1046a is the top section of file 1044a and a handle 1042 is positioned on shank portion 1046a. Smooth shank portion 1046a tapers to square portion 1047a which is between shank portion 1046a and abrading portion 1049a. The taper of the files from the tip ($D_1$) to the diameter at the top of the square portion ($D_3$) remains constant. The tip diameter ($D_1$) of the instruments in this set remains constant while the diameter at the top of the cutting area or abrading portion ($D_2$), is graduated from instrument 1040a to 1040b. An instrument such as file instrument 1040a or a set of file instruments such as 1040a and 1040b comprises a second endodontic instrument means for improving access into the apical root portion after the pulp material has been essentially removed from the operative middle portion by the first endodontic instrument means.

FIG. 15 also depicts set 1070, used to clean the apical portion, as including twelve instruments, 1070a–l, which are configured similarly to instruments 1040a–b. Instruments 1070a–l have a handle 1072 opposite a file 1074. Each file 1074 has a smooth shank portion 1076a, a square portion 1077, an abrading portion 1079 and a file tip 1078. After selecting an instrument from set 1070, the practitioner then determines, based on feel and experience, whether the file is appropriately sized or whether a larger or smaller file is needed. For instance, if the practitioner selects instrument 1070b which has a tip diameter, for example of 0.15 mm, and the file binds after insertion, then the practitioner would switch to instrument 1070a which has, for example, a tip diameter of 0.10 mm. Similarly, if instrument 1070b is too loose then the practitioner would then switch to instrument 1070c which has a tip diameter of 0.20 mm. The practitioner then uses that appropriately sized instrument to clean the apical portion of the root canal by hand. If the practitioner concludes after using an appropriately sized file, that further instrumentation is still needed within the apical portion then the instrument with the next largest file may be used. It is typically unnecessary to use a third instrument with an even larger file after using a series of two instruments. However, the practitioner may clean the apical root portion with a series of more than two instruments as deemed necessary by the practitioner in order to fully clean the apical portion. A file instrument such as file instrument 1070a or a set of file instruments such as 1070a–l comprises a third endodontic instrument means for removing and cleaning essentially all remaining pulp material from the apical root portion after the pulp material has been essentially removed from the operative middle portion. All of the sets of instruments used in this methodology may be sold together as a comprehensive kit or various sets may be grouped together as kits intended for use with teeth of particular lengths.

The present invention provides many benefits and advantages. The dental instrument of the invention allows a single instrument to be used to clean root canals having varying lengths. The present invention also provides for accurate, reliable, and quick adjustment of the working length thereof as used with an appropriate endodontic handpiece. Once set, the working length remains the same throughout an endodontic procedure such as root canal therapy. The handpiece also has a rim which provides an effective stop. These features are particularly advantageous when used to clean the operative middle portion of a root canal being cleaned in the phases described above.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. In a system that includes an endodontic handpiece having a chuck, an improved endodontic instrument which can be secured by the chuck when using the instrument to perform endodontic procedures such as root canal therapy, the improved instrument comprising;

file means for producing an abrasive action for purposes of removing and cleaning pulp material from a root canal during an endodontic procedure, the file means having a proximal end and a distal insertion end; and handle means for defining a plurality of gripping means along the length thereof, each gripping means also serving as a means for indicating the desired working length of the file means relative to the handpiece when the handle means is secured within the chuck.

2. The instrument of claim 1, wherein the handle means includes means for visually identifying the length of the file.

3. The instrument as defined in claim 1, wherein each gripping means includes a uniform length.

4. The instrument as defined in claim 1, wherein at least one of the gripping means has a length that is different from the others.

5. The instrument as defined in claim 1, wherein each gripping means includes a gripping section which has a uniform diameter and cross-sectional shape.

6. The instrument as defined in claim 1, wherein the handle means includes a bevelled section located at a bottom end of the handle means.

7. The instrument as defined in claim 1, wherein the handle means includes gradient markings spaced in increments such that the working length of the instrument can be easily determined by viewing the indicator means.

8. The instrument as defined in claim 1, wherein the handle means includes uniformly spaced gradient markings.

9. The instrument as defined in claim 1, wherein the handle means includes grooves in the handle means which are formed in uniformly spaced increments.

10. The instrument as defined in claim 1, wherein the handle means includes recesses in the handle means which are formed in uniformly spaced increments.

11. The instrument as defined in claim 1, wherein the handle means includes ridges on the handle means which are formed in uniformly spaced increments.

12. In a system that includes an endodontic handpiece having a chuck, an improved endodontic instrument which can be secured by the chuck when using the instrument to perform endodontic procedures such as root canal therapy, the improved instrument comprising:

a file having an abrading portion configured to remove and clean pulp material from a root canal during an endodontic procedure, the file having a proximal end and a distal insertion end which terminates at a tip; and a handle having a top end and a bottom end, the file extending from the bottom end of the handle, and the handle comprising between the top and end bottom ends thereof a plurality of tripping sections, each of which has a predetermined length so that each gripping section also serves as an indicator of the desired working length of the file relative to the handpiece when the handle is secured within the chuck.

13. The instrument of claim 12, wherein the handle has a uniform diameter and cross-sectional shape along its length.

14. The instrument of claim 12, wherein the handle includes means for visually identifying the length of the file.

15. The instrument as defined in claim 12, wherein the gripping sections have a uniform diameter and cross-sectional shape.

16. The instrument as defined in claim 12, wherein the gripping sections have a uniform length.

17. The instrument as defined in claim 12, wherein the handle includes a bevelled section located at a bottom end of the handle, a bottom gripping section adjacent to the bevelled section, and a recess located between the bottom gripping section and another gripping section, and wherein the bevelled section, the bottom gripping section and the recess each have the same length.

18. The instrument of claim 12, wherein the incremental adjustment indicators include gripping sections which have a uniform diameter and cross-sectional shape and which are adapted to be held by a chuck of an endodontic handpiece head in a mated configuration, and wherein the gripping sections are at least half of the surface area of the handle.

19. The instrument as defined in claim 12, wherein the handle includes gradient markings spaced in increments such that the working length of the instrument can be easily determined by viewing the indicators.

20. The instrument as defined in claim 19, wherein the gradient markings are uniformly spaced.

21. The instrument as defined in claim 12, wherein the handle includes grooves in the handle which are formed in uniformly spaced increments.

22. The instrument as defined in claim 12, wherein the handle includes recesses in the handle which are formed in uniformly spaced increments.

23. The instrument as defined in claim 12, wherein the handle includes ridges on the handle which are formed in uniformly spaced increments.

\* \* \* \* \*

UNITED STATES PATENT AND TRADEMARK OFFICE
CERTIFICATE OF CORRECTION

PATENT NO. : 6,213,771 B1
DATED : April 10, 2001
INVENTOR(S) : Dan E. Fischer

Page 1 of 1

It is certified that error appears in the above-identified patent and that said Letters Patent is hereby corrected as shown below:

Column 3,
Line 5, change "time1-consuming" to -- time-consuming --

Column 9,
Line 31, change "do" to -- to --

Column 12,
Line 17, change "10" to -- 110 --

Column 16,
Line 19, after "in" insert -- Serial No. 09/325,125 --

Signed and Sealed this

Sixteenth Day of April, 2002

Attest:

JAMES E. ROGAN
Director of the United States Patent and Trademark Office

Attesting Officer